United States Patent
Mason et al.

(10) Patent No.: US 10,121,389 B1
(45) Date of Patent: Nov. 6, 2018

(54) PROGRESSIVE PREGNANCY WELLNESS PROMOTION USING A PROGRESSION SCHEME AND TASK TRACKING

(71) Applicant: HCA-Information Technology & Services, Inc., Nashville, TN (US)

(72) Inventors: Christopher Mason, Nashville, TN (US); Edmund Fishbough, Nashville, TN (US)

(73) Assignee: HCA-INFORMATION TECHNOLOGY & SERVICES, INC., Nashville, TN (US)

( * ) Notice: Subject to any disclaimer, the term of this patent is extended or adjusted under 35 U.S.C. 154(b) by 0 days.

(21) Appl. No.: 15/620,607

(22) Filed: Jun. 12, 2017

Related U.S. Application Data

(63) Continuation of application No. 14/287,408, filed on May 27, 2014, now Pat. No. 9,715,835.

(60) Provisional application No. 61/827,466, filed on May 24, 2013.

(51) Int. Cl.
```
G09B 19/00      (2006.01)
G06Q 50/22      (2018.01)
G06Q 30/00      (2012.01)
G06Q 10/10      (2012.01)
G06F 19/00      (2018.01)
```

(52) U.S. Cl.
CPC ......... *G09B 19/00* (2013.01); *G06F 19/3481* (2013.01); *G06Q 10/10* (2013.01); *G06Q 30/00* (2013.01); *G06Q 50/22* (2013.01); *G06F 19/3475* (2013.01)

(58) Field of Classification Search
CPC . G09B 19/00; G06F 19/3481; G06F 19/3475; G06Q 10/10; G06Q 30/00; G06Q 50/22
USPC ......................................................... 434/236
See application file for complete search history.

(56) References Cited

U.S. PATENT DOCUMENTS

| | | | |
|---|---|---|---|
| 6,269,339 B1* | 7/2001 | Silver | G06F 19/3456 705/2 |
| 2008/0076637 A1* | 3/2008 | Gilley | G06Q 10/0639 482/9 |
| 2013/0166317 A1* | 6/2013 | Beardall | G06F 19/324 705/2 |
| 2013/0216989 A1* | 8/2013 | Cuthbert | G09B 19/00 434/238 |
| 2014/0045156 A1* | 2/2014 | Alessandri | G09B 19/0092 434/236 |

* cited by examiner

*Primary Examiner* — Robert P Bullington
(74) *Attorney, Agent, or Firm* — Kilpatrick Townsend & Stockton LLP

(57) ABSTRACT

In some embodiments, a scheme engine selects a progressive support scheme that promotes wellness by encouraging users to responsibly respond to a health condition. The scheme includes a set of nodes. Each node represents a progression of the health condition being experienced by a user. A node of the set of nodes is associated with a set of tasks, each promoting wellness given a presence of the condition. A progression tracker identifies, for the user, the node as corresponding to a current progression of the condition. A task engine assigns a weight to a task characteristic based on an input received from the user and selects a task from amongst the set of tasks associated with the identified node. The selection of the task is based on the weight assigned to the task characteristic. The task engine further presents the task to the user.

20 Claims, 18 Drawing Sheets

PROGRESSIVE PREGNANCY WELLNESS PROMOTION USING A PROGRESSION SCHEME AND TASK TRACKING

CROSS-REFERENCE TO RELATED APPLICATIONS

This application is a continuation of U.S. patent application Ser. No. 14/287,408, filed on May 27, 2014, which claims the benefit of and priority to U.S. Provisional Application No. 61/827,466, filed on May 24, 2013. The entire disclosures of the above applications are hereby incorporated by reference, for all purposes, as if fully set forth herein.

BACKGROUND

This disclosure relates in general to methods and systems for utilizing an interactive electronic program to promote users' wellness by, e.g., encouraging the users to complete healthy tasks.

Pregnancies are exciting times but are unfortunately accompanied by the reality that the expecting mother or the expected baby may develop health conditions, such as hypertension, miscarriages, pre-term delivery, mental disabilities, depression, etc. It is thought that many conditions can be managed or even prevented, and the expecting mothers' participation in responsible actions may aid in this effort. Unfortunately, expecting mothers can easily be overwhelmed by the amount of health advice available from various sources, can forget to complete recommended actions or can under-appreciate the importance of some actions.

SUMMARY

In one embodiment, the present disclosure provides a method and system for promoting a user's wellness. A wellness app can access a progressive support scheme, which can relate to a health condition, such as pregnancy, and can present information and activities useful to support the user in her wellness. This scheme can include a set of nodes, and each node can correspond to one or more tasks (e.g., a wellness task, such as a healthy-eating or exercise task, or a virtual engagement task, such as responding to a condition-related question or virtually scheduling a medical appointment) and/or information. Initially, a starting node can be identified for a user based on, for example, a condition state (e.g., current pregnancy duration), an occurrence or risk of one or more complications, a user input (e.g., identifying a preference with regard to condition management) and/or a user location. The user can progress from the starting node along the scheme to one or more other nodes, where the progression (and subsequent node selection) can occur, for example, due to the passage of time, progression of the disease and/or an occurrence of a health complication.

At each node, a corresponding task and/or piece of information can be presented to the user. In some instances, the app provides the opportunity for the user to respond to the task. The response can include an answer to a medical-decision question or an indication as to whether (and/or a degree to which) she completed a wellness task. For example, a wellness task can include drinking several glasses of water in a day, and the user can report that she drank four glasses of water. Responses can influence the user's progression along the scheme. For example, responses can be used to identify a task characteristic that is predictive of whether the user will complete the task, and the progression can depend on the characteristic. As another example, a user's answer to a question (e.g., whether the user is pregnant with one child or with multiple children) can influence the progression. Thus, app presentations made in accordance with the scheme can be customized for the user.

The user can receive virtual rewards (e.g., badges) based on task completions and/or the progression through the scheme. For example, a reward can be presented for full completion of five tasks, the completion of a particular task, having used the app for two months, or having arrived at the beginning of a second trimester. The user can also receive non-virtual rewards, such as coupons or vouchers for particular products. The non-virtual rewards may be automatically presented at time points determined based on a user's current progression through the scheme. Thus, through the app, the user can receive advice, information, tasks and offers that can contribute to improved physical, emotional and/or psychological wellness.

In some embodiments, a scheme engine selects a progressive support scheme that promotes wellness by encouraging users to responsibly respond to a health condition. The scheme includes a set of nodes. Each node represents a progression of the health condition being experienced by a user. A node of the set of nodes is associated with a set of tasks, each promoting wellness given a presence of the condition. A progression tracker identifies, for the user, the node as corresponding to a current progression of the condition. A task engine assigns a weight to a task characteristic based on an input received from the user and selects a task from amongst the set of tasks associated with the identified node. The selection of the task is based on the weight assigned to the task characteristic. The task engine further presents the task to the user.

In some embodiments, a progressive wellness-promotion system is provided for promoting wellness via customized information presentation in a wellness app. A scheme engine selects a progressive support scheme that promotes wellness by encouraging users to responsibly respond to a health condition. The scheme includes a set of nodes, each node representing a progression of the health condition being experienced by a user. A node of the set of nodes is associated with a set of information pieces, each information piece in the set of information pieces identifying information pertaining to the condition. A progression tracker identifies, for the user, the node from the set of nodes as corresponding to a current progression of the health condition for the user. An information engine assigns a weight to an information characteristic based on an input received from the user and selects an information piece from amongst the set of information pieces associated with the identified node. The selection of the information piece is based on the weight assigned to the task characteristic. The information engine further presents the information piece to the user.

In some embodiments, a method is provided for promoting wellness via customized task presentation in a wellness app. A progressive support scheme is identified that promotes wellness by encouraging users to responsibly respond to a health condition. The scheme includes a set of nodes, each node representing a progression of the health condition being experienced by a user. A node of the set of nodes is associated with a set of tasks. Each task in the set of tasks promotes wellness given a presence of the condition. The node is identified for the user from the set of nodes as corresponding to a current progression of the health condition for the user. A weight is assigned to a task characteristic based on an input received from the user. A task is selected from amongst the set of tasks associated with the identified node. The selection of the task is based on the weight assigned to the task characteristic. The task is presented to the user.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes can be made in the function and arrangement of elements without departing from the spirit and scope as set forth in the appended claims.

In one embodiment, the present disclosure provides a method and system for promoting a user's wellness. A wellness app can access a progressive support scheme, which can relate to a health condition, such as pregnancy, and can present information and activities useful to support the user in her wellness. A representation of the user can progress along the scheme due to the passage of time, progression of the disease, an occurrence of a health complication and/or past interactions with the app (e.g., responses to app-presented questions and/or reports related to task completions).

The scheme can include a set of nodes. Each node can correspond to a task and/or a piece of information. When a representation of the user is positioned at a particular node, a corresponding task and/or piece of information can be presented to the user. The user can then interact with the app by, e.g., responding to a question, virtually completing a task and/or reporting whether (and/or when and/or a degree to which) a task was completed.

The user can receive virtual rewards (e.g., badges) based on task completions and/or the progression through the scheme. For example, a reward can be presented for full completion of five tasks, the completion of a particular task, having used the app for two months, or having arrived at the beginning of a second trimester. The user can also receive non-virtual rewards, such as coupons or vouchers for particular products. The non-virtual rewards may be automatically presented at time points determined based on a user's current progression through the scheme. Thus, through the app, the user can receive advice, information, tasks and offers that can contribute to improved physical, emotional and/or psychological wellness. Further, due to user-specific scheme progression, such advice, information, tasks and offered can be selected based on user inputs and/or characteristics.

Figure 1:
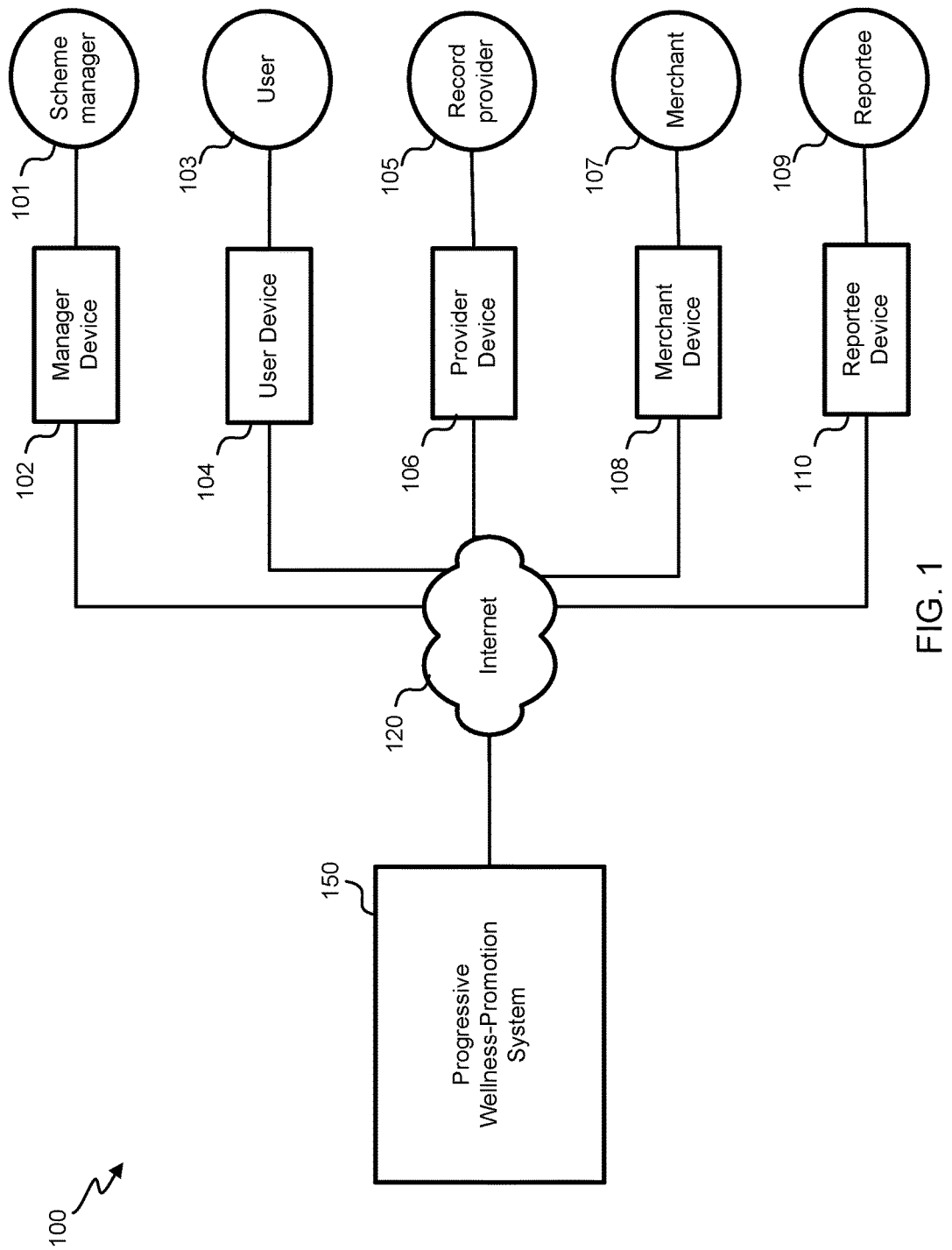
FIG. 1 depicts a block diagram of an embodiment of a wellness-promoting interaction system

Referring first to FIG. 1, a block diagram of an embodiment of a wellness-promoting interaction system 100 is shown. A scheme manager 101, user 103, record provider 105, merchant 107 and/or reportee 109 can interact with a progressive wellness-promotion system 150 via respective devices 102, 104, 106, 108 and/or 110 and a network, such as the Internet 120 or a wide area network (WAN), local area network (LAN) or other backbone. In some embodiments, progressive wellness-promotion system 150 is made available to one or more of scheme manager 101, user 103, record provider 105, merchant 107 and/or reportee 109 via an app (that can be downloaded to and executed on a portable electronic device) or a website. It will be understood that, although only one scheme manager 101, user 103, record provider 105, merchant 107 and/or reportee 109 are shown, system 100 can include multiple scheme managers 101, users 103, record providers 105, merchants 107 and/or reportees 109.

Manager device 102, user device 104, provider device 106, merchant device 108 and/or reportee device 110 can each be a single electronic device, such as a hand-held electronic device (e.g., a smartphone) or a system that includes multiple devices and/or components. The device(s) 102, 104, 106, 108 and/or 110 can include, for example, a computer, such as the desktop computer, a laptop computer, a tablet, smart phone or other electronic device. In some instances, a party 101, 103, 105, 107 and/or 109 uses different devices at different times to interact with the progressive wellness-promotion system 150. For example, user 103 can use a desktop computer initially to set up an account and later use to view a presented task.

Using the progressive wellness-promotion system 150, a scheme manager 101 can identify (e.g., upload, select or partly or fully define) a progressive support scheme. The identification can be performed via a scheme-definition interface, which can accept uploads, identify one or more scheme constraints (e.g., a maximum number of levels), receive scheme parameters, and/or visually represent a scheme (e.g., in a modifiable manner).

Scheme manager 101 can identify a scheme's title, a scheme's applicability (e.g., a medical condition and/or user characteristic corresponding to the scheme), a number of levels, a number of nodes in each of one or more levels, connections between multiple nodes, a node- or level-progression criterion, a task and/or piece of information to associate with each of one or more node, non-virtual rewards, and/or non-virtual rewards and/or reward conditions. In some instances, the scheme identification includes constructing a virtual representation of the scheme (e.g., that represents each node and node connection).

Scheme manager 101 can include, for example, an operator of progressive wellness-promotion system 150, a client of progressive wellness-promotion system 150 (e.g., paying for services of system 150), a physician, or a medical institution.

The progressive support scheme can relate to a condition, such as a medical condition (e.g., pregnancy, diabetes, high blood pressure, surgery, obesity, a combination thereof, cancer, multiple sclerosis, etc.). The scheme's structure can facilitate progression towards a desirable outcome ("the objective") for the condition (e.g., a healthy full-term delivery, reduced blood pressure, full surgery recovery, weight loss, remission, maintained motor function, improved quality of life, etc.). The condition can be associated with a progression, in that a user with the condition may inevitably progress through condition states (e.g., as in pregnancy—progressing across pregnancy time periods) or may possibly progress through condition states (e.g., as in diabetes, cancer of multiple sclerosis—where the disease may be progressing; or as for obesity—where a person may gradually lose weight).

The progressive support scheme can include a series of nodes and can have a linear structure or a multi-directional structure (e.g., a decision-tree structure). A user can be positioned at a node on the scheme (e.g., based on a current condition progression and/or user input) and can progress to another node after, e.g., a period of time has passed, a user has entered data that indicates that a condition has progressed, a record has been received that indicates that new condition information is available, etc. One or more nodes can correspond to a task to present to the user while the user is positioned at the node. The task can be one that is known or suspected to aid in achieving the objective, contribute to the user's future well-begin or be of interest or amusing to the user. Additionally or alternatively, one or more nodes can correspond a piece of information pertaining to the condition to present to the user. The piece of information can include, e.g., information about the biology of the condition (e.g., a recent organ development of a fetus), explanations about tests used to monitor the condition, presentations about condition prevalence, data related to potential medical decisions related to the condition, etc.

The progressive support scheme can further identify rewards and reward conditions. As described further below, a reward can be a virtual reward (e.g., points, badges, etc.) or a non-virtual reward. A non-virtual reward can include an offer for value, such as a voucher, coupon, or discount code. The non-virtual reward can, e.g., include a link to a website and promotion code that can be used by the user to discount purchases within a time period for a fixed percentage. Reward can be presented based on a user's progression through the scheme (e.g., at each trimester) and/or a task completion.

Figure 2A:
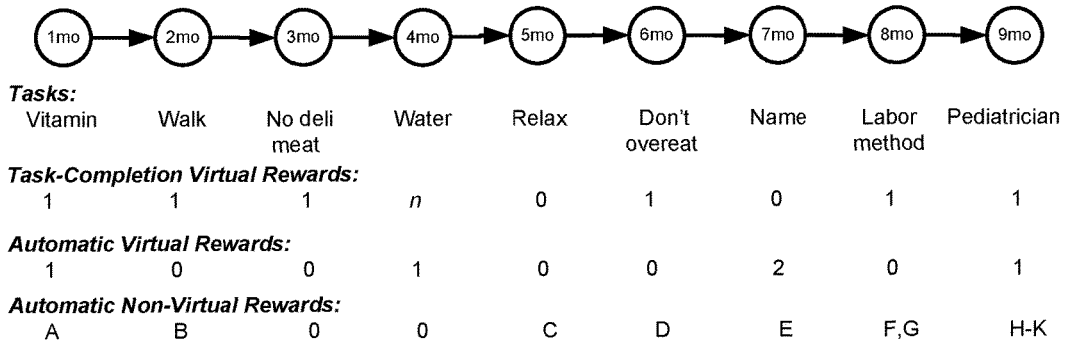
FIGS. 2A-C illustrate representations of three example progressive support schemes.
Figure 2B:
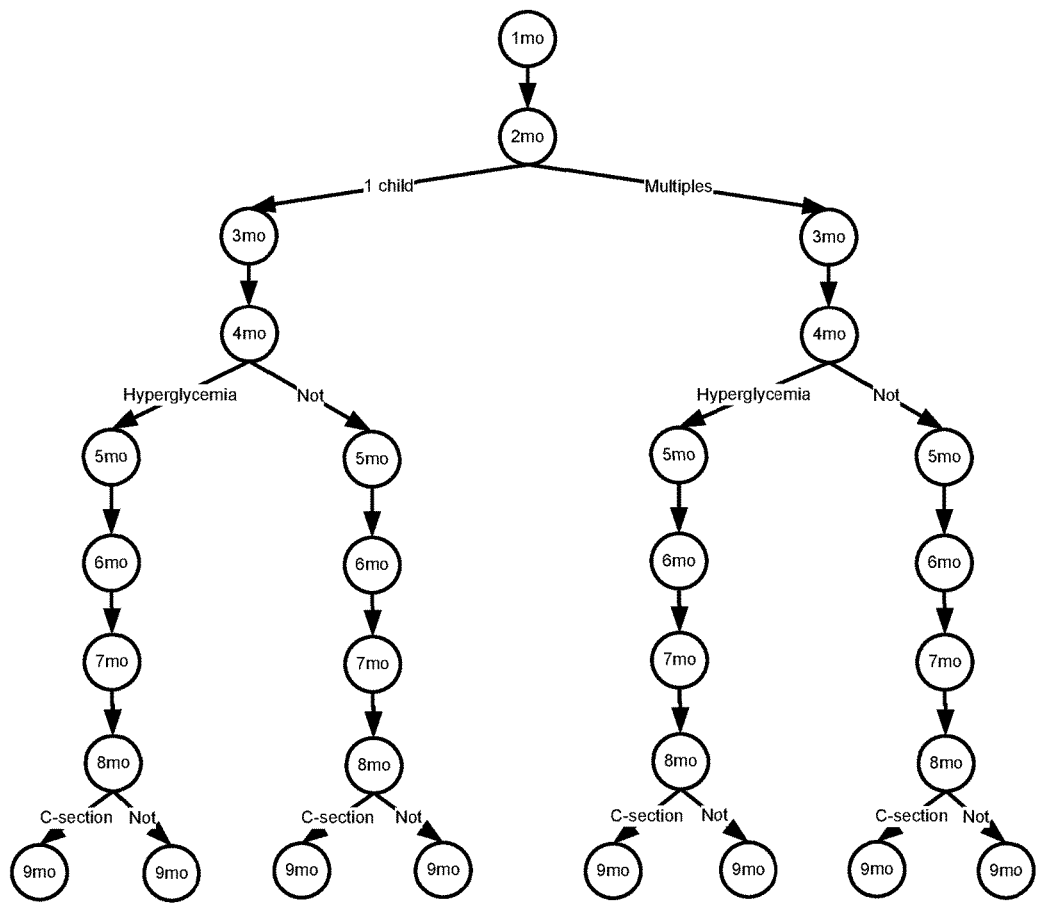
Figure 2C:
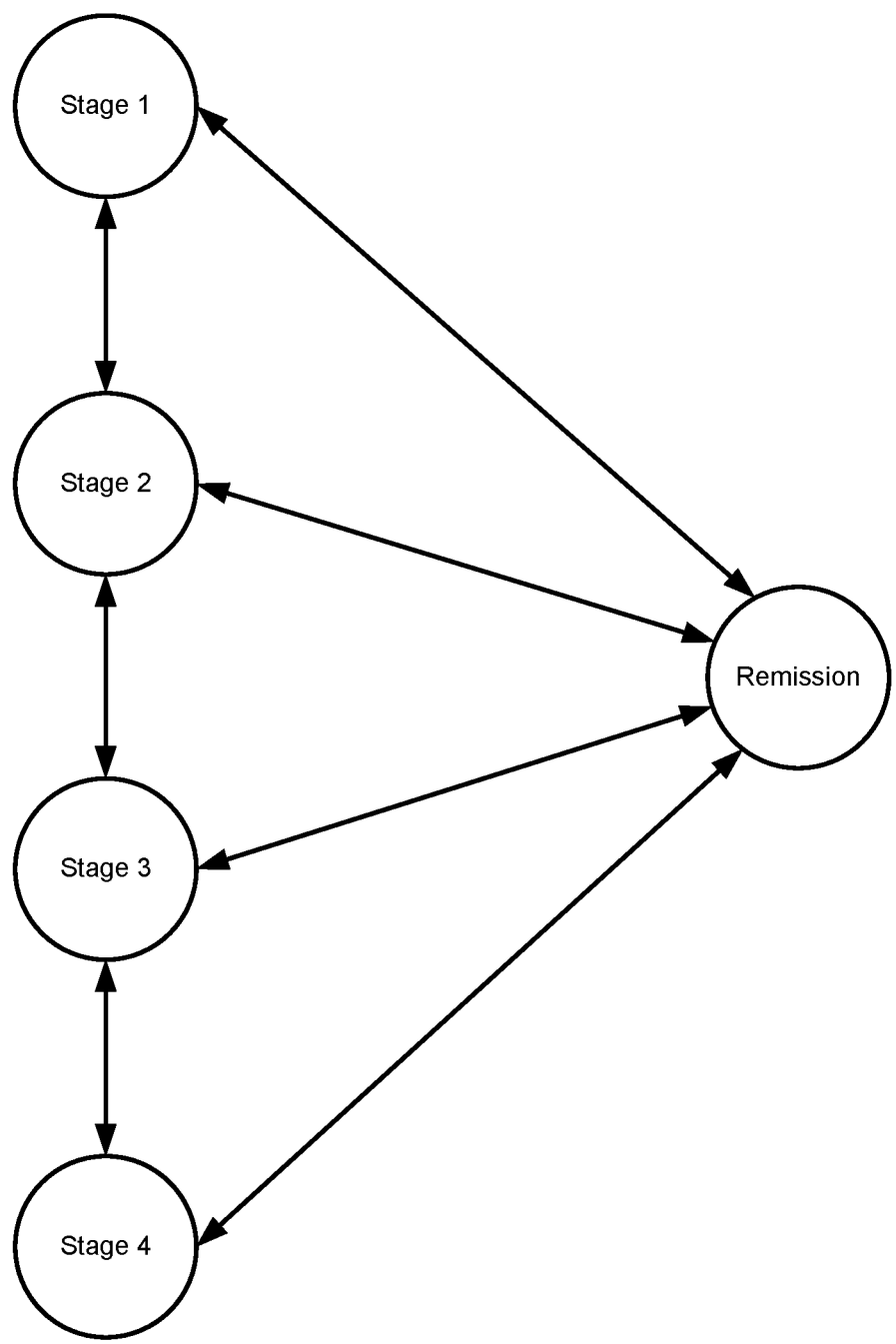

FIGS. 2A-C illustrate representations of three example progressive support schemes. The scheme in FIG. 2A is linear, and the schemes represented in FIGS. 2B and 2C are hierarchical. Thus, a user can only progress along one path in FIG. 2A, while the user can progress along a variety of paths in FIGS. 2B and 2C. The scheme representations in FIGS. 2A and 2B pertain to pregnancy and that in FIG. 2C pertains to cancer.

In FIG. 2A, the scheme includes nine levels, each level having one node, and each node corresponding to a pregnancy month. Thus, a user's initial position in the scheme depends on her pregnancy duration and her progression to subsequent nodes depends on the passage of time. Each of one or more nodes can correspond to a task. For example, in the depicted example, tasks include: take a pre-natal vitamin, take a 10-minute brisk walk, avoid deli meat, drink 8 glasses of water today, relax for 15 minutes, eat fewer than 2200 calories today, choose a name for your baby, make a labor plan, and choose a pediatrician.

Each of one or more nodes can include an indication of a possible or assured reward to present, such as a virtual badge or point. In FIG. 2A, the scheme indicates that a virtual badge is to be presented at the first, second, third, sixth, eighth and ninth nodes only if the user completes the task. At node four, a badge is to be awarded for each glass of water reported to have been drank by the user. Further, a badge is to be automatically awarded (e.g., presented) to the user upon progression to the first, fourth and ninth nodes, and two badges are to be automatically awarded to the user upon progression to the seventh node. The virtual rewards may be transient (e.g., being awarded for a period of time) and/or cumulative. The scheme further includes indications that a non-virtual reward is to be presented at each node except for the third and fourth nodes. Multiple non-virtual rewards are to be presented at the eighth and ninth nodes. The letter indicators identify a particular non-virtual reward to award. Though not shown, each or one or more nodes can also include a piece of information to present to the user.

For simplicity of illustration, the representations in FIGS. 2B and 2C do not include tasks, rewards or information, though it is appreciated that these schemes may include these features. In FIG. 2B, the scheme is hierarchical and includes nine levels. A user can progress downwards through the levels along one of multiple paths. A user's position in the scheme can depend on her pregnancy duration and/or association with particular pregnancy factors.

Specifically, in the illustrated embodiment, which 3-month node the user progresses to or is positioned at depends on whether she is estimated to be having one child or multiple children. Which 5-month node the user progresses to or is positioned at depends on whether she has hyperglycemia or not. Which 9-month node the user progresses to or is positioned at depends on whether she is planning on a caesarian delivery or a natural delivery. An estimated child number, hyperglycemia presence or delivery plan can be automatically identified based on received medical records or identified based on input from the user.

In FIG. 2C, the scheme's nodes relate to stages of cancer. Thus, the user is not guaranteed to progress across levels following a mere passage of time. Rather, progression depends on whether a user's cancer has progressed to a new stage or entered remission. Unlike FIGS. 2A-2B, the scheme in FIG. 2C include multiple potential paths, in that a use does not necessarily progress through the nodes in single direction (e.g., rightwards or downwards).

It will be appreciated that schemes can be simpler, more detailed and/or more complex than those illustrated in FIGS. 2A-2C. For example, a pregnancy scheme can include a different node corresponding to every day throughout a pregnancy (e.g., and potentially extending for a time period beyond the pregnancy). Further, there need not be a one-to-one assignment of information or tasks to a given node. For example, one node can include five tasks, all of which or a pseudo-randomly selected one(s) of which can be presented to a user. As another example, some nodes can include no information to present to the user.

Returning to FIG. 1, a user 103 can actively or passively set up an account with progressive wellness-promotion system 150. For example, a user 103 can provide information about herself or information can be extracted from data in records provided by a record provider 105. The information can be collected at a single time or at multiple times. The information can be then used to create an account.

Using the provided information, progressive wellness-promotion system 150 can identify a position for a representation of user 103 along a progressive support scheme and can thereafter present user 103 with tasks, information and/or rewards based on the scheme. In some instances, the information can be used to select a progressive support scheme (e.g., based on a current or potential medical condition, medical-care provider and/or user preference). The account can be updated based on, for example, user input (e.g., identifying account or profile information, responding to a question and/or reporting whether, when and/or to what extent a task was completed), records provided by record provider 105, automatically detected data (e.g., based on a sensor measurement detected by user device 104 and/or other data. Updated account data can, in some instances, be used to modify the position for the representation of user 103, which can thereby influence (for example) what tasks and/or information are presented to the user. In some instances, in addition to or instead of influencing a position of the representation of user 103, account data can influence a selection of or generation of a task, an information piece and/or a reward to present or offer to the user. For example, multiple tasks and/or information pieces can be associated with a single node, and a subset of those available can be selected for presentation to a particular user based on account data.

Record provider 105 can provide records such as an electronic medical record, medical-record data or test result (e.g., ultrasound summary, MRI summary, blood-test result, etc.). Record provider 105 can be, e.g., a physician, medical institution or lab technician. The record can be a text file or a standard format. In some instances, provider 105 interacts with an interface to identify specific information. For example, a provider 105 can select a test type from a pull-down menu, enter numeric data (e.g., indicating a baby's head circumference, a baby's estimated weight, an expectant mother's weight, an expectant mother's blood pressure, an expectant mother's blood count, etc.) and type in a physician's note. In some instances, records are automatically sent, e.g., following a test or at routine intervals. In some instances, progressive wellness-promotion system 150 requests a record from record provider 105 (e.g., upon a user indicating that she recently had a medical test).

A merchant 107 can identify non-virtual reward offers that can be presented by progressive wellness-promotion system 150 to a user 103. Merchant 107 may be able to access part or all of a scheme. In some instances, progressive wellness-promotion system further provides merchant 107 with summaries of users 103 using system 150 (e.g., a number of users at various levels, a percentage of users who previously redeemed various types of offers, a number of users in various age groups, a percentage of users who completed various tasks, etc.).

Merchant 107 can identify the reward, a reward-presentation condition (e.g., a task that must be completed, a user characteristic (such as an identified hobby from a list of hobbies), a time period for presenting the reward to a particular user, a time period for presenting the rewards to qualified users, etc.), and/or a node or level in the scheme at which the reward is to be presented. For example, in the scheme represented in FIG. 2B, a merchant 107 can identify a reward as being a 20% discount to a diapers website, the reward to be presented to all users upon their progression to a 9mo (i.e., level 9) node, and to the reward to include a code that can be redeemed within two months from the date that it was presented to the user. As another example, a merchant 107 can identify a reward as being a coupon to attend up to one month of yoga classes at a gym to all users who identified exercise as an interest and who completed a relaxation task.

In some instances, rather than merchant 107 providing a reward to offer, merchant 107 can identify an advertisement to present. Merchant 107 can upload an image, audio track and/or video track for the presentation. Merchant 107 can identify an advertisement-presentation condition and/or a node or level at which the advertisement is to be presented.

A merchant 107 can submit a payment to offer the reward or progressive wellness-promotion system 150 can transfer payment to merchant 107 in exchange for being able to offer the reward. In some instances, progressive wellness-promotion system 150 receives a payment from merchant 107 based on a number of users who redeemed a respective offer and/or an characteristic of the redemption (e.g., an amount purchased on a website using a percentage discount).

A reportee 109 is an entity to receive a report with data about users of progressive wellness-promotion system 150. The report can identify data pertaining to a specific user and/or a group of users. For example, a report can identify tasks completed by a particular user and/or how much time a user spent logged onto system 150. A report can include group data such as user demographics, a completion rate of various user groups of one or more tasks, and/or progression characteristics of users. Data pertaining to one or more users may be anonymized, partly anonymous or user identifiable. For example, a report can indicate that 5 of 10 users using the app and reporting to be 27 weeks pregnant completed the associated task.

Reportee 109 can include any party receiving data related to an interaction of a user (e.g., a non-reportee user) with progressive wellness-promotion system 150. Reportee 109 can include, e.g., a physician, a physician assistant, and/or an entity at a medical institution. In some instances, reportee 109 can include an employer, an insurance company, etc. An employer or insurance company may then be able to reward an employee's or insured's task completions (e.g., with cash or discounted premiums). These rewards can be presented via progressive wellness-promotion system 150 or independently. In some instances, a reportee 109 is a user or a merchant.

Figure 3:
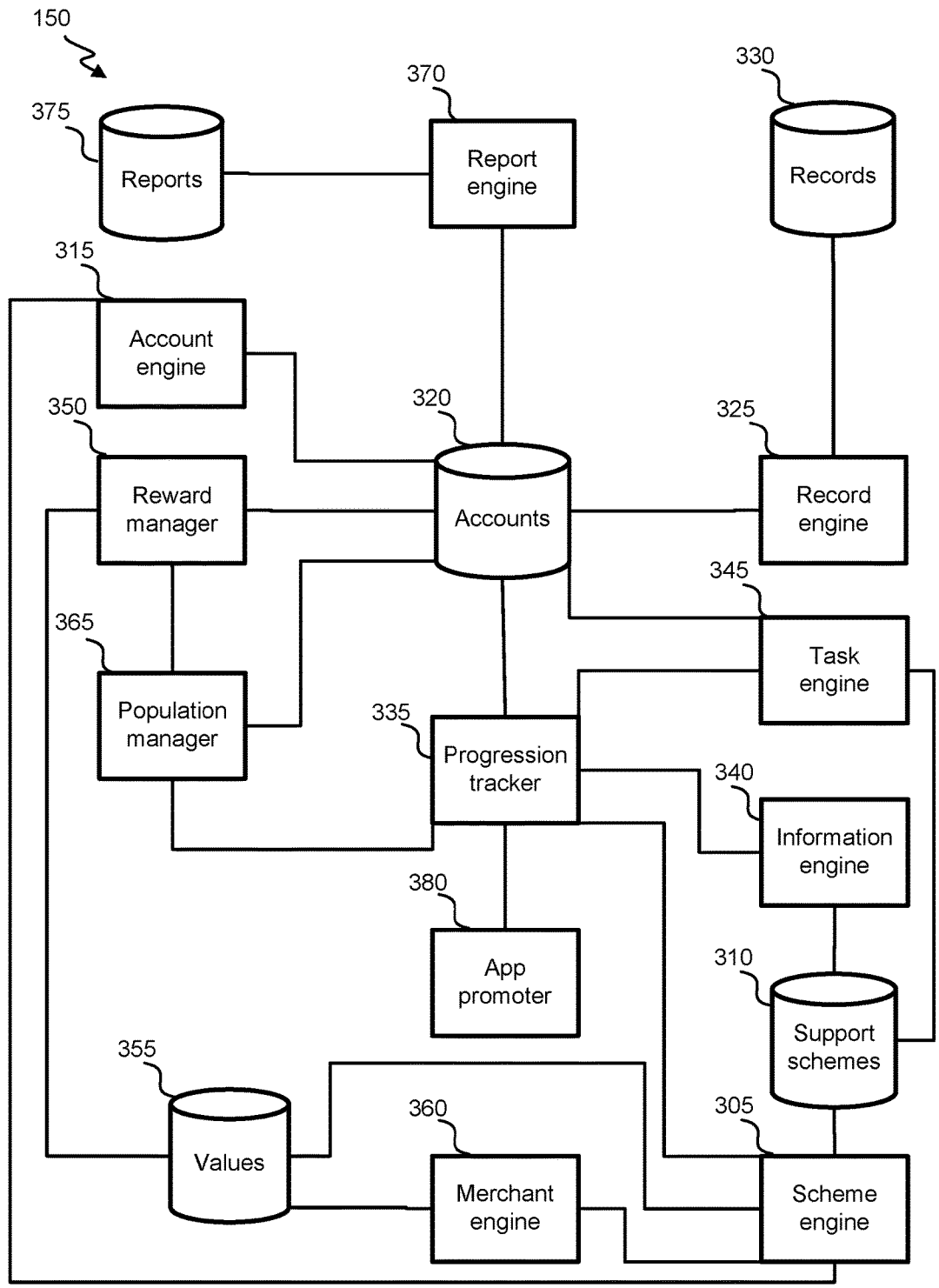
FIG. 3 depicts a block diagram of an embodiment of a progressive wellness-promoting system.

Referring next to FIG. 3, a block diagram of an embodiment of progressive wellness-promotion system 150 is shown. Progressive wellness-promotion system 150 can be, in part or in its entirety, in a cloud. In some instances, at least part of progressive wellness-promotion system 150 is present on a device, such as a user device 104. For example, a progression tracker 335 can be on user device 104, and a scheme engine 305 can be in a cloud. In some instances, part of a component (e.g., part of reward manager 350) resides in a cloud and another part of the component resides in a device. Thus, progressive wellness-promotion system 150 can include a distributed system.

Progressive wellness-promotion system 150 includes a scheme engine 305, which collects specifications from a scheme manager 101 indicative of properties of a scheme. The properties can include specifications about when a scheme should be used (e.g., a pertinent health condition), a structure of a scheme (e.g., a number of levels, a number of nodes in general, a number of nodes in each of one or more levels, connections between nodes, possible paths between nodes, criteria for user placement at a node, and/or criteria for moving between nodes) and/or node data (e.g., association with one or more tasks, association with one or more pieces of information), associated criteria for awarding one or more reward points, indications as to how many reward points are to be awarded, etc.

Scheme manager 101 can provide some or all of the scheme specifications by, e.g., selecting an option (e.g., identifying a scheme structure), entering a value or text into a field (e.g., to identify a number of levels or to identify a piece of information to present when a user representation is positioned at a particular node), interacting with an interface (e.g., to construct a layout for the nodes) and/or uploading a file. Scheme engine 305 can verify an identity of scheme manager 101 (e.g., by verifying a username and password) prior to accepting scheme specifications. Scheme engine 305 can aggregate specifications for a particular scheme together, format the aggregated specifications in a standardized manner, and store the formatted data as a support scheme in support-scheme database 310. Scheme engine 305 can subsequently allow a same or different scheme manager 101 to modify the scheme.

Progressive wellness-promotion system 150 includes an account engine 315 which (e.g., using input provided by a user 103, data automatically collected from a user device and/or using input identifying the user but provided by other entities, such as a medical-care entity) generates an account that includes account information for user 103. The account can be generated prior to or after user 103 downloads, installs or executes an app or other software provided by progressive wellness-promotion system 150. In some instances, the account generation is conditioned upon receipt of specific types of input. For example, account engine 315 can restrain from generating an account if a user has not provided an email address. In some instances, account engine 315 generates an account no matter what data has been provided by a user. Thus, e.g., a blank account can be generated for a user providing no information. This blank account can nevertheless include some data, such as cookie information, an IP address, a download number, an operating-system identifier, etc. Account engine 315 can then supplement the blank account to include user-provided information upon receipt of that information.

Account database 320 can, for each account, store data pertaining to the associated user 103. The stored data can include, for example, identifying information, contact information, a history of interactions with system 150, payment information and/or user preferences. Once an account is created, a user can access the account by entering login information. Alternatively, such login information can be saved, or cookies can be utilized such that the user is always or typically (e.g., until cookies are cleared or a security event is detected) logged in while using a particular device.

User preferences can include preferences pertaining to types of tasks to present (e.g., physical exercise tasks, relaxation tasks, psychological wellness tasks, preparatory tasks, nutrition tasks, etc.), types of information to present (e.g., development information pertaining to an unborn baby, statistical information about a current stage in the condition (e.g., a percentage of expecting mothers who experience nausea at week 8 in pregnancy), statistical information about a future stage in the condition (e.g., a distribution of which weeks expecting mothers deliver at), biological-mechanistic information pertaining to the condition, etc.) and/or types of rewards to offer (e.g., types of products which the user would like discounts for, a style of virtual badge, etc.). In some instances, a preference relates to a condition. For example, a preference can identify a goal for an outcome of the condition and//or a goal for managing the condition (e.g., whether the user intends to take medications during pregnancy and/or whether the user intends to have a natural birth or C-section). In some instances, a preference includes a restriction (e.g., only present exercise tasks or do not present nutrition tasks). A preference can include one explicitly identified by a user or a learned preference. For example, it can be determined that a user prefers planning tasks and/or decision-making tasks as compared to exercise or dietary tasks based on previously presented tasks and users reported completions.

Examples of account information includes a user's name, email address, credit card information, home address, phone number, occupation, employer (e.g., and the employer's address, phone number and/or email address), insurance company (and the company's address, phone number and/or email address) and/or an insurance member or group identifier. Account information can identify non-user party (e.g., an emergency contact, insurance subscriber) and contact information for the non-user party. Account information can also include login information, which can include a username (which may be an email address) and a password.

Account information can include information pertaining to one or more medical entities. For example, account information can include a name of a physician or medical group, a name of a hospital, a phone number for a medical entity, an address for a medical entity, an email address for a medical entity and/or a fax number for the medical entity. In some instances, a user particularly identifies the medical entity. In some instances, one or more medical entities are automatically identified based on, for example, a process that is biased towards entities with an address near the user, having a specialty corresponding to a condition that the user is known or inferred to have, and/or accepting an insurance of the user.

Account information can further include medical information. The medical information can identify and/or characterize a user's condition and/or a history of the condition. The condition can include a medical condition, such as pregnancy, obesity, hypertension or a disease (e.g., cancer or diabetes). The medical information can indicate how long a user has had or been diagnosed with the condition, a current progression (e.g., in terms of time, disease progression or condition severity) of the condition, any complications of the condition (e.g., hyperglycemia or pre-term labor), any current medications being taken or treatments being received for the condition, any symptoms currently or previously experienced by user 103, any physicians or institutions currently or previously treating user 103 for the condition or for other conditions, an identification of other health conditions or health events (e.g., surgeries) experienced by user 103, an identification of health conditions experienced by family members of user 103. Medical information can further include a user's height and weight, sex, race and/or behavior patterns (e.g., estimated frequency and amount of alcohol intake, non-prescription drug use, and/or exercise). Medical information can include an identification of a test (e.g., blood test, ultrasound, MRI, x-ray, etc.) taken by user 103, a date of the test, and/or a result of the test (e.g., a blood count, estimated baby head circumference, estimated baby length, estimated baby weight, estimated due date, etc.).

In some instances, account engine 315 receives the medical information from user 103. In some instances, a record engine 325 receives the medical information via a record from a record provider 105. Record provider 105 can use fields in an interface to provide the record and/or can provide the record by uploading a file (e.g., an image file and/or a text file). In some instances, the received data is processed by record engine 235 (e.g., to extract and/or convert one or more values). Record engine 325 can store the provided record (or a processed version thereof) in record database 330. Record engine 325 can identify an account associated with the record. Record engine 325 can then link the account to the record.

In some instances, record engine 325 can require that user 103 gives permission to accept the provided record prior to storing the record, linking the record to the user's account and/or adding extracted record data to the account. This permission can include a permission pertaining to a specific record, a permission pertaining to all records from a particular record provider 105 and/or an identification of a record provider 105. In one instance, user 103 identifies a record provider 105 (and may further identify a test data and/or type), and record engine 325 requests a record from the identified record provider 105. In some embodiments, the providing of a record by a record provider initiates a generation of an account by account engine 315. Account engine 315 may then contact an identified patient (i.e., user) to request account information and/or provide login information such that she can access the account.

Scheme engine 305 can select a support scheme for a user. In some instances, a same scheme is selected for all users and/or all users using a particular app. Alternatively, a scheme from a plurality of schemes can be selected based on a user's medical information, a user's preferences, usage criteria of one or more schemes, a medical entity associated with a user's account (e.g., an identified doctor for the user), and/or which app or software was downloaded by the user.

A progression tracker 335 can then determine a user's current progression, which can include identifying a position (e.g., node) within the selected scheme for the user. In some instances, the position includes an initial position (which can initially be a current position). The initial position can be selected based on, for example, node definitions, a condition state (e.g., pregnancy duration), a user's medical information, a user preference, date, condition objective of a user and/or associated medical entity. In some instances, the position includes a current position and/or progression across positions. The current progression can be determined based on node definitions within a scheme, the user's medical information, a current time, a user's self-reporting pertaining to a condition state, another party's reporting pertaining to a condition state of the user, and/or user inputs (e.g., identifying decisions responsive to medical-treatment options, reporting with regard to task completions, etc.). For example, a scheme can include a node for every day throughout pregnancy. Progression tracker 335 can then identify a current node for a user based on the user's estimated conception date or due date.

An information engine 340 can identify (e.g., select, collect and/or generate) a piece of information, and/or a task engine 345 can identify a task given the user's current progression (e.g., by identifying a piece of information and/or task for an identified node). It will be appreciated that a "piece of information" identified by information engine 340 need not be assuredly accurate (e.g., but can instead include an estimate of a baby's development, a widely accepted biological mechanism, etc.). One or both of the piece of information and task identifications can include selecting between multiple pieces of information and/or tasks of a given node, e.g., using a pseudo-random selection technique or based on a user's preferences (e.g., preferring specific types of information and/or tasks). In some instances, the selection can be based on a user's prior self-reported interest in a piece of information, a population of users' self-reported interest in a piece of information, a user's prior self-reported completion (or lack thereof) of a task, or a population of users' self-reported completion of a task. For example, task engine 345 can avoid selecting a weight-lifting task for a node based on a user's failure to report completion of any previously presented weight-lifting tasks, or task engine 345 can select a task to eat a serving of fish that day based on the fact that 95% of users previously presented with that task completed it.

In some instances, a piece of information is identified by collecting data from a remote source and/or generating new statistics, visualizations, summaries, etc. For example, information engine 340 can access data identifying inputs from a set of users as to their plans to deliver a baby in the hospital versus at home. Information engine 340 may then determine a portion of users planning to deliver their babies in a hospital. As another example, information engine 340 can access data from a hospital that identifies, for a set of patients, a labor characteristic (e.g., epidural usage) and birth outcome (e.g., baby's hospital stay duration). Information engine 340 can then separately process the data based on the characteristic and can identify, for example, a distribution of statistic of the birth outcome for each characteristic.

For a pregnancy-focused progression scheme, information pieces can include information pertaining to a pregnancy, a delivery, post-partum care for a woman and/or care or health of a baby. Exemplary information pieces can relate to, for example, benefits of breastfeeding, breastfeeding tips, prevalence of SIDS or SUIDS, risk factors for SIDS or SUDS, health benefits of administering vitamin K to a baby, health benefits of administering erythromycin eye drops to a baby, car seat safety tips, car seat regulations, jaundice prevalence, jaundice screen information, recommended pediatrician consults, doctor (e.g., OB/GYN or pediatrician) recommendations, a tip for interviewing a doctor, vaccine benefits, vaccine information, and/or potential post-partum health issues. In some instances, the information pieces presented can be tailored given a medical provider associated with a user. For example, an information piece can identify a characteristic, option or requirement (e.g., a post-delivery hospital discharge requirement) of a delivery ward in a hospital close to or selected by a user. In some instances, the information pieces are provided by a medical provider associated with a user and/or are based on data associated with a group of users.

Information engine 340 can present the identified piece of information and/or task engine 345 can present the identified task to the user. The piece of information and/or task can be presented via a webpage, an app page, an email or a text message. The piece of information and/or task can be unconditionally presented (e.g., irrespective of whether a user opens an app or views a webpage, such as when the piece of information and/or task are included in a transmitted email) or can be presented only upon a user's explicit or implicit request for the piece of information and/or task (e.g., upon opening an app, clicking on an option to receive a task, etc.). The number of tasks and/or pieces of information identified and presented can be fixed (e.g., to one a day) or variable (e.g., presenting a new piece of information and/or task each time a user requests one and/or presenting a number of tasks and/or pieces of information as specified by a user). The task and/or piece of information can be presented simultaneously or independently. In some instances, a potential reward is identified during a presentation of a task. For example, a number "3" can indicate that a user will receive three points upon completing the task, or a faded virtual badge can indicate that a user will be awarded upon the task completion.

Task engine 345 can receive an indication from user 103 as to whether a presented task was completed, when it was completed and/or an extent of the completion. In some instances, it is assumed that the task was not completed absent any indication from the user to the contrary. Completion can be assessed in a binary (e.g., complete or not) or non-binary manner (e.g., a number of minutes walked by the user). Thus, user 103 can identify her completion of a task by merely selecting a completion option or by describing the completion (e.g., entering a number).

Task engine 345 updates the user's account to reflect assigned tasks, completed tasks and/or a degree of completion. It will be appreciated that this reflection can also indicate uncompleted tasks, as those that were assigned but not completed can be assumed to be uncompleted. In some instances, a user is given a specific (e.g., fixed) time period to report that an assigned task has been completed.

A reward manager 350 can determine whether a user has satisfied a criterion for a reward and, if so, can distribute the reward. The criterion can be identified from a support scheme and can include a user-characteristic criterion, a progression criterion and/or a task-completion criterion. For example, exemplary criterion for a virtual badge include that the user completed a particular task at any time, any exercise task within the past two weeks, or three tasks out of five tasks presented within the past three days. As other examples, the criterion for award of a product discount can be that the user resides in Virginia and progressed to a level-six node in the scheme, or that the user progressed to a particular node in the scheme, is currently located in Virginia (e.g., estimated based on a GPS location of user device 104) and completed her first assigned task at that node.

In some instances, if a reward's criterion is satisfied, the reward is automatically awarded. In some instances, the award depends on other factors. For example, there may be ten non-virtual rewards, each with a criterion that the user is to have just progressed to an eight-month node in a pregnancy scheme. A system criterion can limit the number of non-virtual rewards to be awarded at a given time to be three or less. Thus, reward manager 350 can select three of the ten non-virtual rewards based on a pseudo-random selection, which providing merchants pay the most commission, which non-virtual rewards were most recently added to value database 355, which non-virtual rewards have been most frequently redeemed by users, etc.

Virtual rewards can be awarded by, e.g., adding points to a point score in the user's account or adding a badge to a badgeboard in the user's account. The user can then view her awarded badges and/or points via an interface to system 150. For example, an interface can show a set of badges, some of which are earned and brightly colored and the rest of which have not (e.g., yet) been earned and are faded. Reward manager 350 can inform user of the award, e.g., by announcing the award to the user on an account page (e.g., of a website or app), in an email sent to the user, or in a text message sent to the user. In some instances, the award is not announced though the user can become aware of the award by viewing a reward section, e.g., of an account page.

Reward manager 350 can access values from value database 355 to determine whether and what non-virtual rewards to award the user. The non-virtual rewards can include a reward of value, such as a discount or voucher. The non-virtual reward can include a code and/or a link to a website such that it is easy to electronically transmit to the user and easy for the user to redeem the reward. The non-virtual reward can include restrictions, such as a minimum purchase or an expiration date.

Various merchants 107 can add non-virtual rewards to value database 355 via communication with a merchant engine 360. Merchant engine 360 can ensure that a merchant is approved to add a value (e.g., based on a permission associated with a merchant's account). The merchant can be one paying to have its value(s) presented, agreeing to pay a fee based on users who visit the merchant's website following presentation of its value(s), or agreeing to pay a fixed fee or commission based on users who purchase a product or service using a presented value. In some instances, merchant engine 360 solicits a value from a merchant.

A verified merchant can be allowed to identify a value, a criterion for awarding the value, information to present with the value (e.g., a website or company name to present with the value), a format for presenting the value (e.g., a company logo or an HTML code), any restrictions on use of the value (e.g., an expiration date or minimum purchase amount and/or any global restrictions on the value (e.g., not awarding the value more than n times, not awarding the value more than once to a single user, etc.).

Progressive wellness-promotion system 150 can include a population manager 365 that aggregates data and computes a statistic characterizing account access, a health characteristic (e.g., weight, blood pressure, blood count, baby's head circumference, baby's kick count, etc.), task presentations, task completions, reward awardances and/or reward redemptions for a group of users. The group can include all users or a group having a shared characteristic (e.g., having a due date in a same season, having a similar age, having a similar task-type preference). The aggregation can be performed across all users in the group or a subgroup of the users (e.g., those with a similar medical history absent consideration of the condition at issue). The aggregation can further account for distinct stages in the condition. For example, the aggregation can group instances (e.g., account access, task presentations, etc.) that occurred within a same time period in users' pregnancies. The statistic can include a median, mode, mean, error, standard deviation, and/or distribution. For example, a statistic can indicate that, at weeks 8-10 in pregnancy, 85% of users accessed their account, each of those users were presented with a 'take-a-brief-walk' task, 70% of those users reported completing the task, and the reported walk time was rather normally distributed around a mode of 15 minutes. As another example, a statistic can include a distribution showing the amount of weight gained (based on self-reported user weights) by users between weeks 4 and 20 of their pregnancies.

Population manager 365 can further compare a characteristic of a particular user to a comparable characteristic of the group. For example, population manager 365 can compute a distribution showing resting heart rates of users in their $30^{th}$ week of pregnancy and can overlay a symbol or vertical line at a horizontal location indicative of a particular user's resting heart rate in her $30^{th}$ week of pregnancy. As another example, population manager 365 can indicate that, of the users who have been using system 150 for a length of time similar to that of a user, 70% of those users have completed more tasks than the user.

In some instances, a reward criterion is based on a population analysis performed by population manager. For example, a badge can be awarded only if the user is in the top 10% of a group of users in terms of total task completions.

Progressive wellness-promotion system 150 can include a report engine 370 that generates a report to provide to one or more reportees 109. The report can be stored in a report database 375. The report can include information specific to a user and/or information for a group of users. The report can identify account access, a health characteristic (e.g., weight, blood pressure, blood count, baby's head circumference, baby's kick count, etc.), a presented task, a completion of the task, an awarded reward, and/or whether the reward was redeemed.

For example, the report can indicate that a pregnant user logged into her account 15 days out of the last 45 days, that her weight has gradually changed from 150 to 170 pounds (a weight change 5% above the average change for a group of users), that she has been presented with 30 tasks and reported completing 20 of them and that recent medical records provided by her obstetrician indicate that there are no known pregnancy complications to date. The report can be transmitted (e.g., electronically, such as in the form of an email) to reportees, such as a user herself, a user's physician (e.g., general practitioner or obstetrician), a user's hospital, a user's insurance company, or a user's employer. The user may have previously given permission to send the report to the reportee(s). In some instances, the user's identity and/or specific information is obscured. For example, the user may be identified by a number, and rather than identifying a specific weight gain or number of completed tasks, these characteristics can instead be identified as being appropriate.

Report engine 370 can analyze account-access information, health information and/or task-completion information to determine whether the user should be rewarded by a reportee (e.g., by receiving a bonus from an employer or premium discount from an insurance company). The report can then identify the user, identify that a bonus or discount is to be given and/or identify an amount for the bonus or discount.

In some instances, a generated report reflects only population-level data (generated by population manager 365) and does not include information characterizing a specific user characteristic. Generation of the population-level data can include generating one or more correlations. The correlations can be between any two (or more for a high-dimensional analysis) of: an initial user health characteristic (e.g., weight), a non-health user characteristic (e.g., age or task-type preference), condition complication (e.g., occurrence of hyperglycemia), activity pattern (e.g., median self-reported daily calorie consumption or median self-reported exercise duration), account access, presented task, potential task-completion reward, self-reported task completion, reward redemption, and/or health result (e.g., a "healthy delivery and baby" as reported by a record provider 105 via a record or as self-reported by a user 103). The report can then be transmitted (e.g., electronically) to physicians, medical institutions, an operator of progressive wellness-promotion system 150, a government agency or one or more users. In some instances, the report is transmitted to a merchant, which may aid the merchant in understanding a demographic and/or interest of a user base and historical reward efficacy.

The reports can reflect, for a single user of group of users, a degree of user engagement with system 150, a degree of effort to complete wellness tasks, a type of task most likely to be completed by users, an initial health characteristic (e.g., weight or blood count), a subsequent health characteristic, a trend in a health characteristic, a correlation between a completion of a type of wellness task and an improvement in a health characteristic, a correlation between an improvement in a health characteristic and obtaining a primary objective, a correlation between offering various rewards and task completions, etc. A reportee can use this information to understand pertinent history for a given user, estimate a likely history for a user based on population patterns, recommend a task likely to be completed by a given user or group of users, recommend a task likely to lead to a positive wellness consequence, establish an effective reward system, etc.

In some instances, progressive wellness-promotion system 150 can include an app promoter 380 that presents a promotion for another app or program to the user at select times. The promotion can identify the other app, include a description of the app and include an option for a user to download the app or otherwise register or obtain access to the other app. The promotion can be presented at time based on a user's progression. For example, a promotion can be presented when a user reaches a node for week 30, week 35, week 38 and week 39 of her pregnancy. The promotion can include a discount for purchasing the other app and/or can offer to transfer some or all information from the user's account to the other app.

The other app can be related to an app or website provided by progressive wellness-promotion system 150. Specifically, each app can pertain to related health conditions. For example, an app provided by system 150 can pertain to pregnancy, and the other app can pertain to motherhood or infants. As another example, an app provided by system 150 can pertain to weight loss, and the other app can pertain to weight maintenance. In some instances, an app can be simultaneously of interest to a user. For example, after determining that a pregnant woman has hyperglycemia via a pregnancy app, a diabetes app can be promoted. In some instances, both apps are controlled and/or operated by a same entity.

Figure 4:
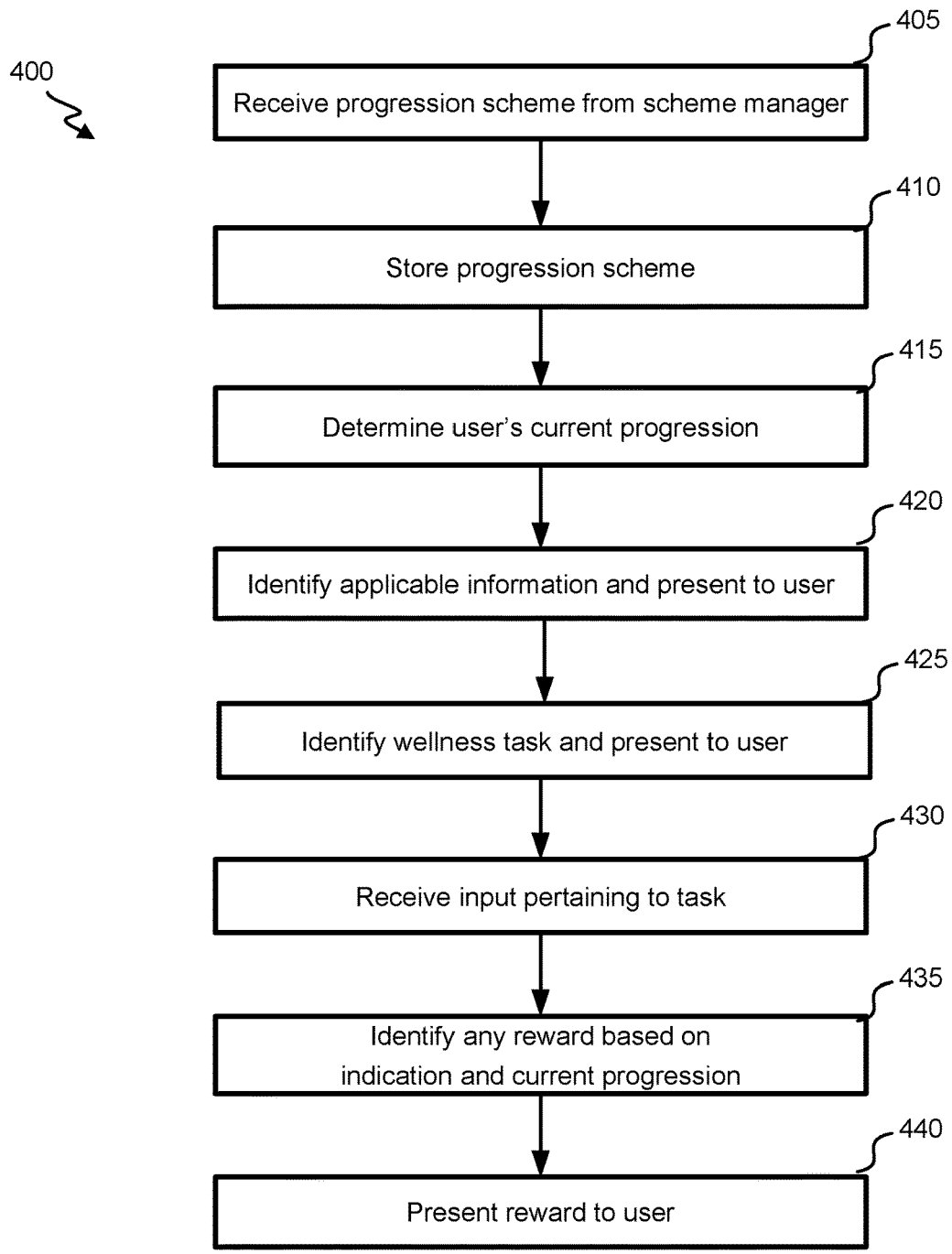
FIG. 4 illustrates a flowchart of an embodiment of a process for using progressive wellness-support scheme to identify wellness tasks and information to present to a user.

FIG. 4 illustrates a flowchart of an embodiment of a process 400 for using progressive wellness-support scheme to identify wellness tasks and information to present to a user. Process 400 begins at block 405, where scheme engine 305 receives a progression scheme from scheme manager 101. Receipt of the scheme can include receiving the entire scheme or receiving scheme characteristics, which scheme engine 305 can use to generate a scheme. Scheme engine 305 stores the progression scheme in a support-scheme database 310 at block 410. The scheme can then be used, e.g., for all users, all users who downloaded a particular app, all users who selected the scheme, all users with a particular health condition (e.g., pregnancy), etc.

Using the progression scheme, progression tracker 335 determines a current progression of a user 103 at block 415. The current progression can be an initial progression or a subsequent progression. The progression can be determined based on placement criteria of nodes in the schemes, such that determining the progression includes identifying a node for user 103. The criteria can relate to, e.g., temporal progression of a condition (e.g., 4 months pregnant), condition complication occurrence (e.g., hyperglycemia), condition stage (e.g., stage-4 cancer), etc. User information (e.g., health information provided from user 103 or obtained from a record) can be used to determine which node criterion is met.

Based on the scheme and current progression, task engine 345 identifies a wellness task and presents the task to user 103 at block 420. Based on the scheme and current progression, information engine 340 identifies applicable information and presents the information to user 103 at block 425. For example, a user can be "positioned" at a node after it is determined that the node represents the user's progression, and the task and piece of information(s) can be included in the node.

Task engine 345 receives input from user 103 pertaining to the presented task. In some instances, the input includes an indication from user 103 as whether, when and/or how the task was completed at block 430. For example, if a task was to spend time relaxing, to spend 15-30 minutes relaxing or to spend 15 minutes relaxing, the user can indicate that she completed the task and spent 30 minutes relaxing. An absence of receiving a task-completion indication from a user can be assumed to indicate that the task was not completed. In some instances, providing the input itself is partial or full completion of a task. For example, a task can include completing a survey, answering a question, electronically scheduling an appointment (e.g., using an app), At block 435, reward manager 350 determines any reward to be awarded based on the input received at block 430 and/or the current progression determined at block 415. The reward can be a virtual and/or non-virtual reward. In some instances, virtual rewards are awarded for task completions and non-virtual rewards are awarded based on a current progression. In some instances, a reward (e.g., magnitude or whether it is a virtual or non-virtual reward) depends on whether a task completed by a user was a reported physical task or a virtual task (e.g., responding to questions, reading information and/or scheduling an appointment).

An identity and/or magnitude (e.g., quantity of reward points) of the reward can depend on which task(s) were completed, how many tasks were completed, an extent of task completion and/or a current progression. The reward can be identified based on the scheme (e.g., having a node that identifies a specific potential reward) or based on a value database that identifies awardance criteria. Reward manager 350 presents reward to user 103 at block 440. For example, the reward can be added to an app page or webpage (e.g., on a badgeboard and/or account page), can be emailed to user 103 and/or can be sent via a text message to user 103.

Figure 5:
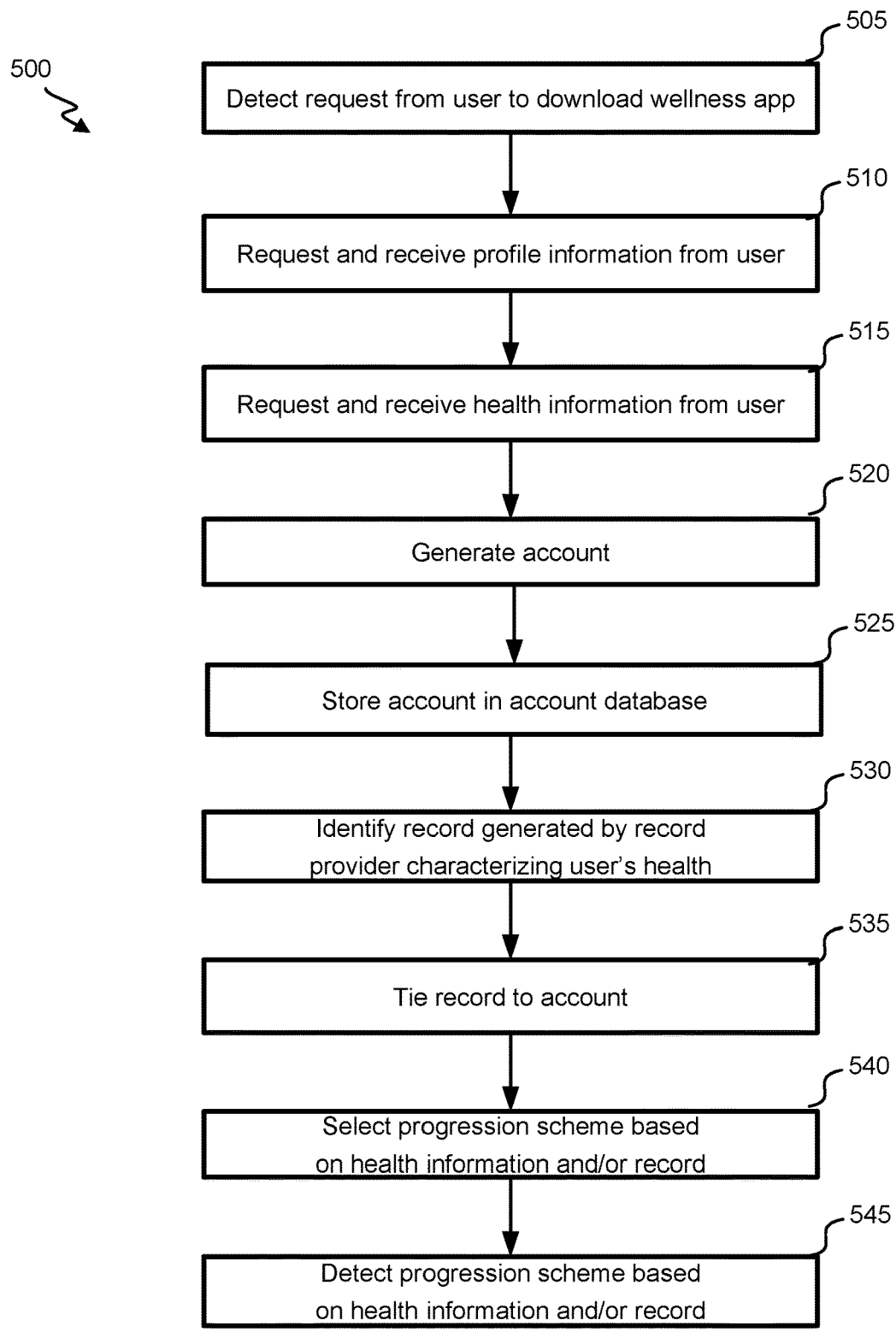
FIG. 5 illustrates a flowchart of an embodiment of a process for presenting a progressive wellness-support scheme to a user.

FIG. 5 illustrates a flowchart of an embodiment of a process 500 for presenting a progressive wellness-support scheme to a user. Process 500 begins at block 505, where account engine 315 detects a request from a user 103 to download a wellness app. Account engine 315 requests and receives profile information from user 103 at block 510. The profile information can include, e.g., identification information and/or login information. Some or all of the information may be required to set up an account. Account engine 315 requests and receives health information from the user at block 515. Account engine 315 generates an account at block 520. The account can include the health and profile information. Account engine 315 stores the account in account database 320 at block 525.

Record engine 325 identifies a record generated by a record provider 105 and characterizing the user's health at block 530. In some instances, record engine 325 first detects submission of the record by record provider 105 and then identifies which user it pertains to. Record engine 325 ties the identified record to account at block 535. For example, data can be extracted from the record and added to the account, the entire record can be added to the account, an identifier of the record can be added to the account or a table can associate the account and record.

Scheme engine 305 selects a progression scheme (e.g., from support-scheme database 310) based on user-provided health information and/or record at block 540. For example, if the user is pregnant and overweight, a scheme can be selected that addresses these conditions. In some instances, only one scheme is available, such that that scheme is automatically selected. Scheme selection can also or alternatively depend on user preferences and/or specified wellness objectives. For example, different schemes may be selected depending on users' views with regard to preventative medical treatment, risk assumption, natural therapies, etc.

In some instances, schemes in a set of schemes pertaining to a condition can vary with respect to a scheme structure (e.g., hierarchical or linear, split points in a hierarchy, number of nodes in a given or all levels, number of levels and/or connections between nodes). As another example, schemes in a set of schemes can vary with respect to node definitions, node- or level-progression criteria and/or other factors that could influence positioning of a representative of a given user in the scheme. Accordingly, which scheme is selected may depend on, for example, a user's physician (e.g., which may be associated with a particular definition for one or more nodes or a progression criteria), a user's observed or predicted access patterns (e.g., such that a more discretized and/or detailed scheme may be selected for a user frequently accessing an app).

Progression tracker 335 detects a current progression based on progressions scheme and on user-provided health information and/or record at block 545. The current progression can be an initial or subsequent progression. Subsequent progressions can be determined, e.g., independently or based on the initial progression and a time passage, user inputs or recent record data. The progression can be stored in the user's account and/or can influence information, tasks and/or potential rewards presented to the user. In some instances, progression tracker 335 regularly, periodically or routinely (e.g., after each login or app opening for a user) determines a current progression. Each progression can then be stored in the user's account.

Figure 6:
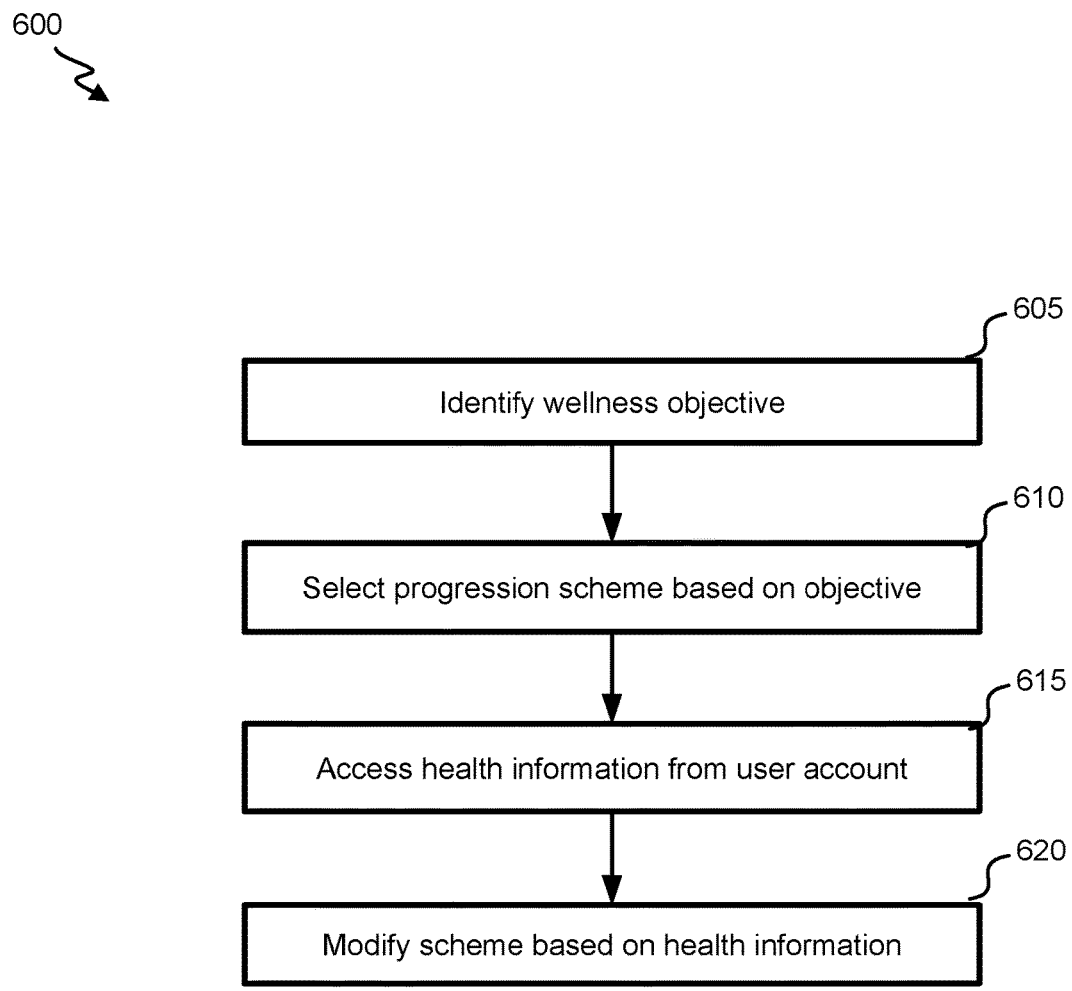
FIG. 6 illustrates a flowchart of an embodiment of a process for modifying a support scheme based on a user's health data.

FIG. 6 illustrates a flowchart of an embodiment of a process 600 for modifying a support scheme based on a user's health data. Process 600 begins at block 605, where scheme engine 305 identifies a wellness objective. The wellness objective can be one selected by or identified by a user 103, one identified based on a user's health condition (identified based on user-provided or record-provided health information), or one associated with a particular app or website. Scheme engine 305 selects a progression scheme based on the objective at block 610.

Account engine 315 accesses health information for a user (provided by the user or determined from a record) from the user's account at block 615. The health information can include, e.g., a user's weight, a condition complication, a test result (e.g., high white-blood cell count), etc.

Scheme engine 305 modifies the progression scheme based on the health information at block 620. In some instances, modifying the progression scheme includes modifying a task- and/or information-selection protocol to use for the scheme. For example, each of one or more nodes in a progression scheme can be associated with a set of tasks and/or pieces of information. Each of some or all of the tasks and/or pieces of information can be tagged with a characteristic (e.g., a difficulty ranking, a statistical-emphasis rating, one or more categorizations, an empirical user completion statistic, and/or a time-commitment rating). A protocol can identify how (e.g., and/or when) to select amongst the tasks and/or information associated with the node. The protocol can include utilizing a pseudo-random selection and/or focusing the selection based on the task and/or information characteristics.

In some instances, modifying a task- and/or information-selection protocol can include constraining a selection to and/or biasing a selection towards tasks and/or information having a particular characteristic (e.g., only selecting tasks that can be performed immediately, biasing toward forward-looking information, or restricting dietary tasks to vegetarian-compliant tasks). As another example, modifying a task- and/or information-selection protocol can include constraining a selection to avoid and/or biasing a selection away from tasks and/or information having a particular characteristic (e.g., not presenting information with statistics, biasing away from tasks with low difficulty rankings or not presenting information pertaining to pregnancy and/or birth with multiples). As yet another example, modifying a task- and/or information-selection protocol can include identifying and/or modifying a number or frequency of presentations of information and/or tasks to present (e.g., which can include how many pieces of information to present relative to tasks) and/or a variability in types of tasks and/or information to present.

Tasks, information and/or potential rewards to be presented can be altered to promote wellness given the health information. For example, low-calorie tasks, nutrition facts and gym-membership offers can be presented to users with high weights, or low-salt-intake tasks, stress information and relaxation offers can be presented to users with high blood pressures. In some instances, the selected scheme has a set of tasks, information and/or potential rewards associated with each of one or more nodes, not all of which are to be presented. A selection of a task, piece of information and/or potential reward for user presentation can then be biased at block 620 based on the health information. In some instances, the modification at block 620 includes directing a user's progression through the scheme or using a different scheme with a different structure and/or node identities.

Figure 7:
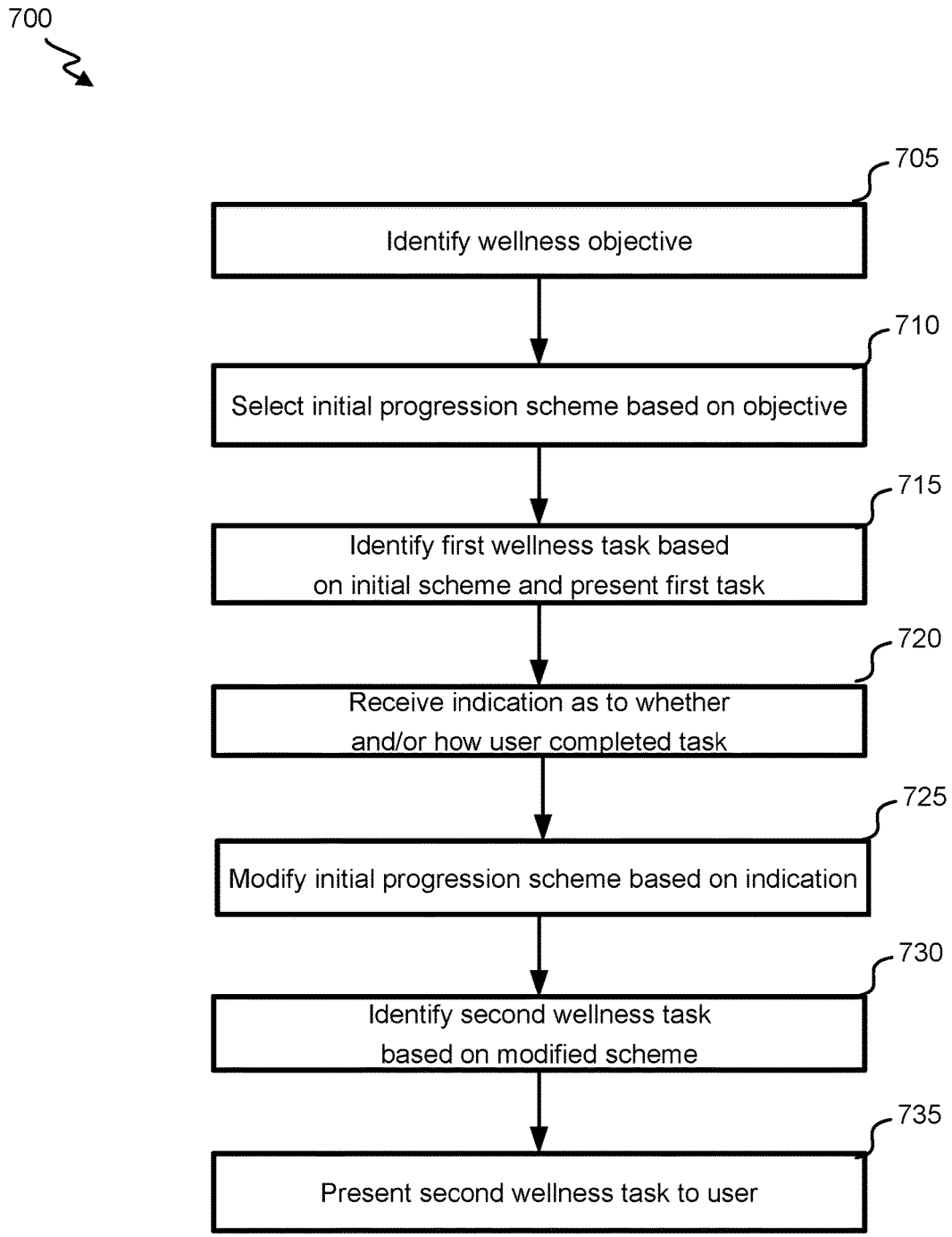
FIG. 7 illustrates a flowchart of an embodiment of a process for using user-reported task completions to modify a support scheme.

FIG. 7 illustrates a flowchart of an embodiment of a process 700 for using user-reported task completions to modify a support scheme. Process 700 begins at block 705, where scheme engine 305 identifies a wellness objective. Scheme engine 305 selects an initial progression scheme based on the objective at block 710. Task engine 345 identifies a first wellness task based on the progression scheme at block 715. For example, progression tracker 335 can identify a user's current progression and a node for that progression, and task engine 345 can select or identify a task from the node. Task engine 345 presents the first wellness task to a user 103 also at block 715. Task engine 345 receives an indication from user 103 as whether and/or how the first task was completed at block 720.

At block 725, scheme engine 305 modifies the initial progression scheme based on the indication. This modification can include modifying a task-selection protocol. For example, the modification can include biasing task presentations towards or away from a type of task that has been infrequently (e.g., in terms of absolute number or relative to other task types) completed by user 103, or to change (e.g., change a type, increase or decrease a quantity and/or increase or decrease a value) of a potential reward. Task engine 345 identifies a second wellness task based on the modified progression scheme at block 730. Task engine 345 presents the second wellness task to user 103 at block 735.

Figure 8:
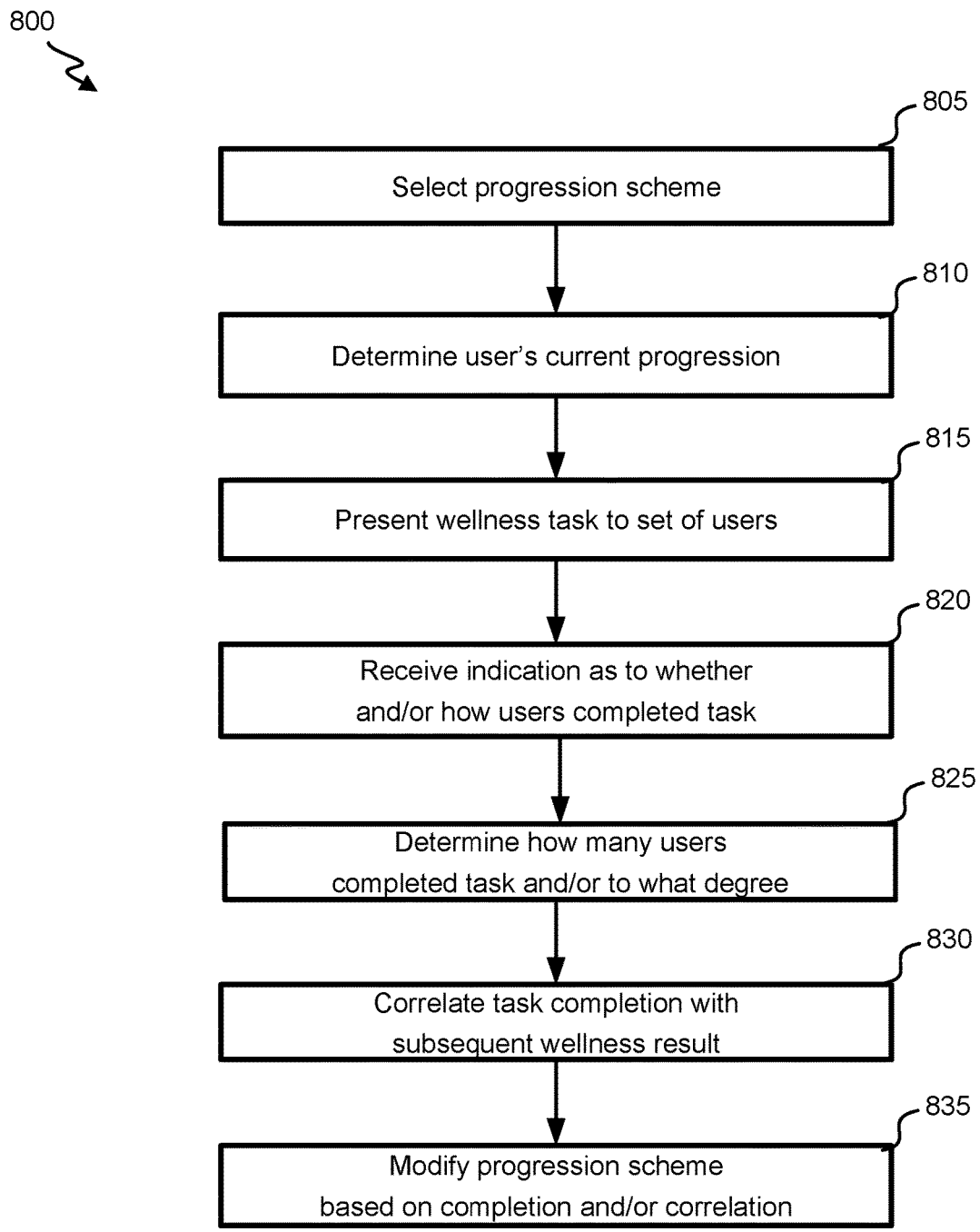
FIG. 8 illustrates a flowchart of an embodiment of a process for using user-reported task completions to modify a support scheme.

FIG. 8 illustrates a flowchart of an embodiment of a process 800 for using user-reported task completions to modify a support scheme. Process 800 begins at block 805, where scheme engine 305 selects a progression scheme from support-scheme database 310. Using the progression scheme, progression tracker 335 determines a current progression of user at block 810.

Task engine 345 presents a wellness task to set of users at block 815. The wellness task can be one of a particular node or one in a set of nodes, and the set of users can be users positioned (e.g., simultaneously or at different times) at the node(s). Task engine 345 receives an indication from each of the users as whether and/or how the task was completed at block 820. A lack of a completion indication can be interpreted as meaning that the user did not complete the task.

Population manager 365 determines how many users completed the task and/or a degree to which users completed the task at block 825. For example, population manager 365 can determine that 90% if users completed a walking task, with 50% of those users walking under one mile, 25% walking 1-2 miles and 25% walking 2 or more miles.

Population manager 365 correlates task completion with a subsequent wellness result at block 830. In one instance, the subsequent wellness result is an indication as to whether a user met a wellness objective (e.g., healthy delivery, desired weight loss, reduced blood pressure, etc.). In one instance, the result is an intermediary result, such as whether a user maintains healthy weight and blood pressure in her sixth month of pregnancy, or whether a user remains on track to his weight-loss goal. In one instance, the result is an indictor of wellness, such a high kick count being one indicator of an in-utero healthy baby. The wellness result can be binary or not. For example, the result can be an amount of weight loss could be a non-binary result. The correlation can produce a significance variable (e.g., a p-value) and/or a magnitude variable (e.g., an R or $R^2$ variable). High significance and/or magnitude variables (e.g., low p-values and high $R^2$ values) can indicate a correlation.

Scheme engine 305 modifies the progression scheme based on the completion and/or correlation at block 835. For example, those task types for which task completions are correlated with positive wellness results can be preferentially presented. As another example, tasks that users are likely to complete can be preferentially presented (e.g., rather than presenting a beneficial task which users are unlikely to complete). In some instances, a multi-dimensional analysis or model can be used to identify tasks or task types that are likely to lead to positive wellness results (which can account for a probability of completion). The analysis and/or modification can be performed globally for all users or can be performed in a manner specific to user characteristics. For example, an analysis or modification can be performed separately for users of various age groups, or an analysis itself can identify user characteristics that influence the correlation or completion measure(s).

In one instance, task clusters are formed. Tasks in a given cluster can include those likely to be performed by a particular group of users. For example, if a user performs (in general or preferentially relative to other tasks) Tasks A-D assigned to a cluster, it may be predicted that the user will also perform the other tasks in the cluster. The progression scheme can then be modified for the particular user to bias towards selection of tasks assigned to the cluster.

Figure 9:
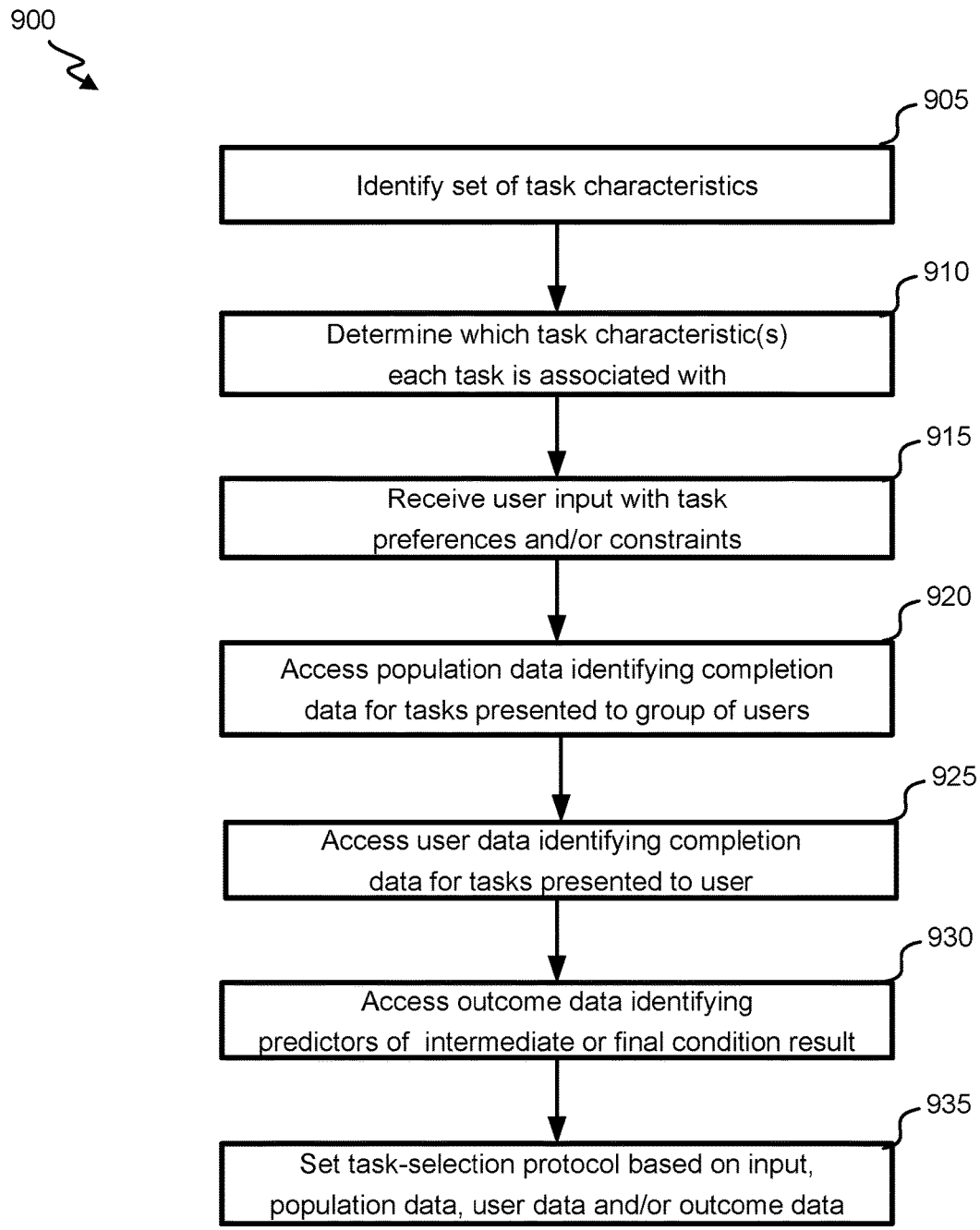
FIG. 9 illustrates a flowchart of an embodiment of a process for modifying a progression scheme based on modification of a task-selection protocol.

FIG. 9 illustrates a flowchart of an embodiment of a process 900 for modifying a progression scheme based on modification of a task-selection protocol. Process 900 begins at block 905, where task engine 345 identifies a set of task characteristics. In some instances, at least some of the task characteristics are mutually exclusive. In some instances, at least some of the task characteristics are not mutually exclusive. The task characteristics can be identified, for example, based on input from a scheme manager and/or provider of one or more tasks. A task characteristic can include, for example, an estimated completion time, an estimated completion effort, a skill level, whether the task is an exercise task, whether the task is a nutrition task, whether the task is a virtual task, whether the task is a planning task, whether the task is a question-answering task, whether the task involves coordinating with or communicating with another party, whether the task is a social task, etc.

At block 910, task engine 345 determines, for each of one or more tasks, which task characteristic(s) the task is associated with. The determination can be performed based on, for example, one or more tags for the task, a keyword detection in the task and/or a source of the task.

Task engine 345 receives user input with a task preference and/or task constraint at block 915. The preference or constraint can be a positive one (e.g., identifying a task characteristic that all tasks assigned to the user are to have or to bias tasks towards those with the characteristic) or a negative one (e.g., identifying a task characteristic that no tasks assigned to the user are to have or to bias tasks away from those with the characteristic). A preference can include a scaled response. For example, a user can identify a ranking (e.g., from 1-10) for a task characteristic, can order various characteristics in terms of preference, and/or can assign a weight to each of one or more characteristics.

At block 920, population manager 365 accesses population data identifying completion data for each task in a set of tasks. For example, for each task, it can be determined— for instances where the task was presented to a user—what the probability was that the user completed the task or reported task completion. As another example, the population data can correspond to an average completion time (e.g., based on a presentation time). The population data can be determined based on data corresponding to a group of users. The group of users can correspond to all users, users having been presented a task within a defined time period, users with a particular user characteristic, users associated with a threshold app engagement, etc. Based on the performance of block 820, task engine 345 can identify, for example, a task characteristic that is associated with a high completion probability and/or a task characteristic associated with a low completion probability. Alternatively or additionally, based on the performance of block 820, task engine 345 can identify, for example, one or more particular tasks associated with a high completion probability and/or one or more particular tasks associated with a low completion probability.

At block 925, task engine 345 accesses user data identifying completion of tasks presented to a user. The user data can identify, for example, how many tasks the user completed (e.g., in a time period or total), which tasks the user completed, which tasks the user did not complete, a completion time period (e.g., from task presentation until completion or a report of completion) for each of one or more tasks, and/or an extent of completion for each of one or more tasks. In some instances, a result of a task can be identified. For example, for a task requesting that a user answer one or more questions, a result can include an answer. As another example, for a task requesting that a user complete an online condition self-assessment quiz, a result can include a self-assessment score.

At block 930, population manager 365 accesses outcome data identifying one or more predictors of intermediate or final condition results. For example, a predictor may include a health attribute (e.g., a weight or blood pressure), a user decision (e.g., opting to accept a vaccine, co-sleeping with an infant), a medical event (e.g., induction), a behavior characteristic (e.g., exercise frequency, alcohol intake patterns), etc. A predictor can be associated with one or more task characteristics. For example, if a predictor of labor complications is being obese, a related task characteristic can include a categorization of being an exercise task.

Based on the input, population, data, user data and/or outcome data, a task-selection protocol can be set at block 935. Setting the protocol can include adjusting a previous or default protocol. The protocol can be set to, for example, abide by user-input constraints, bias task selection according to user-input preferences, bias towards selection of tasks with high group-completion rates, bias towards selection of tasks having a characteristic associated with a high group-completion rate, bias towards selection of tasks having a characteristic associated with a high user-completion rate, and/or bias towards selection of tasks having a characteristic associated with a positive intermediate or final condition result.

In one instance, based on the accessed user data, a user is assigned to a group. Population data and/or outcome data for that group can then be analyzed to identify tasks likely to be completed by and/or effective (e.g., in terms of achieving a positive intermediate or final condition result) for the group and/or one or more task characteristics predictive of task completion and/or efficacy. Task selection for the user can then be biased towards or restricted to those identified tasks and/or tasks associated with the one or more task characteristics.

In some instances, a task-selection protocol includes selecting one or more task characteristics for a given user and then biasing a task selection towards task with the one or more task characteristics and/or requiring that a selected task be associated with the one or more task characteristics.

In one instance, for a given user, each of one or more task characteristics is assigned a weight (e.g., based on data or input as discussed herein), and each task is assigned a score based on its association with each of the one or more task characteristics (e.g., which may be binary or non-binary) and the task-characteristic weight(s). A task selection can then include, for example, pseudo-randomly selecting a task from amongst those assigned an above-threshold score, selecting a top- or high-score task that has not been presented to a particular user before, etc.

A task characteristic can relate to, for example, a type of task (e.g., exercise, answer-completion, nutrition, medication or vitamin administration, or appointment attendance or scheduling), an intensity or difficulty of the task, a time commitment of the task, an interaction aspect of the task (e.g., whether the task can be completed without involvement of others), a popularity of a task (e.g., which may, or may not, be conveyed to a user—which itself could be a task characteristic), an efficacy of a task with regard to an effect on an intermediate or final condition result or condition or medication side effect or symptom (e.g., which may, or may not, be conveyed to a user—which itself could be a task characteristic), and/or a framing of a task. As an example of how a task can be characterized by framing, a first task could include: "To reduce the risk of complications during pregnancy, perform 20 minutes of light exercise each day for (at least) a week." Another, differently framed, task could include: "To improve the likelihood of a smooth and natural delivery, perform 20 minutes of light exercise each day for (at least) a week."

Figure 10:
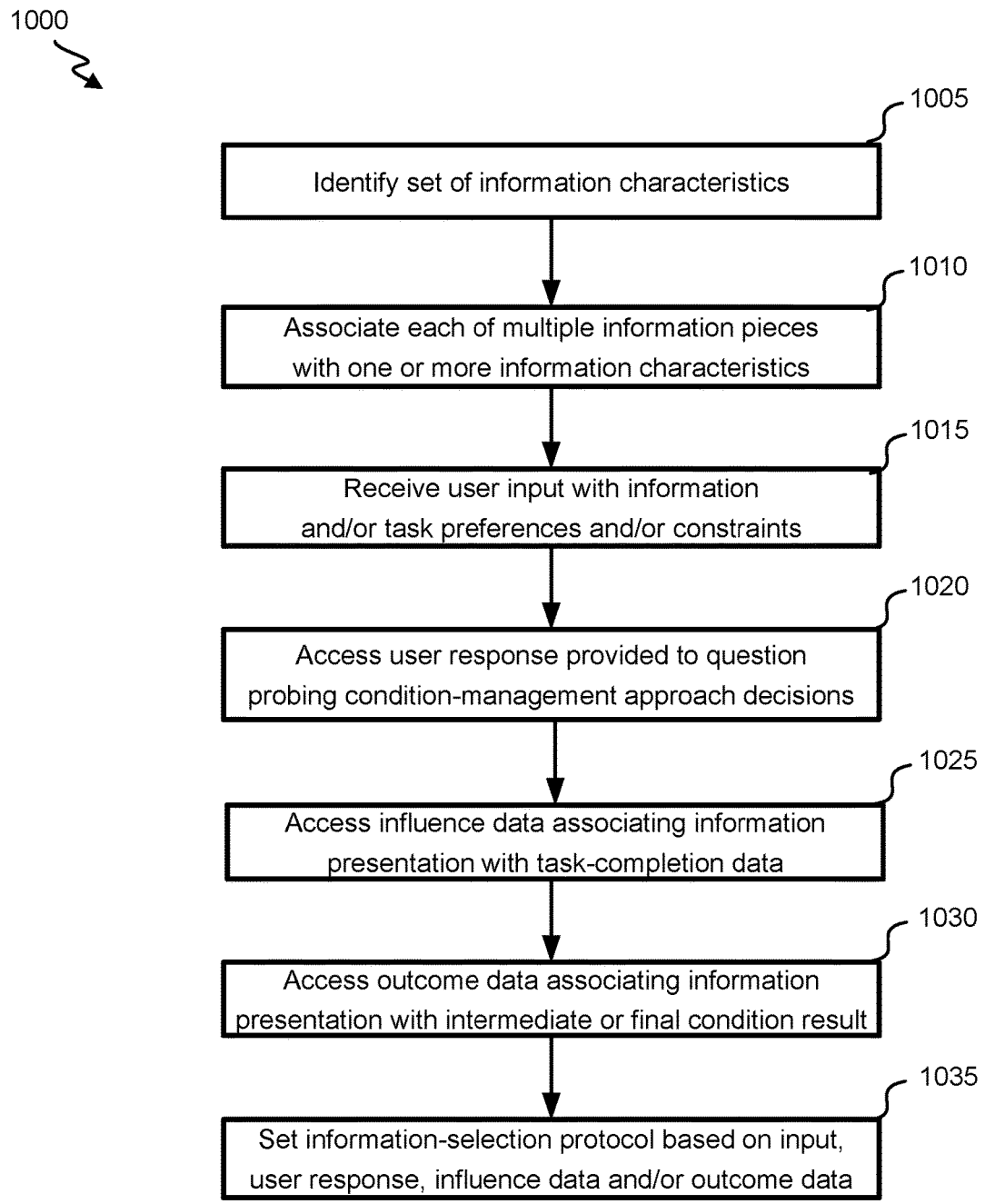
FIG. 10 illustrates a flowchart of an embodiment of a process for modifying a progression scheme based on modification of an information-selection protocol.

FIG. 10 illustrates a flowchart of an embodiment of a process 1000 for modifying a progression scheme based on modification of an information-selection protocol. Process 1000 begins at block 1005, where information engine 340 identifies a set of information characteristics. In some instances, at least some of the information characteristics are mutually exclusive. In some instances, at least some of the information characteristics are not mutually exclusive. The information characteristics can be identified, for example, based on input from a scheme manager and/or provider of one or more pieces of information. An information characteristic can include, for example, whether data is included in the reference (and/or a type of data), whether scientific research is referred to, who the information pertains to (e.g., a pregnant woman or her baby), whether the information identifies a population statistic (e.g., identifying decisions made by other users or patients), whether the information highlights potential benefits (e.g., of completing a recommended task or selecting a recommended practice) or potential drawbacks (e.g., of not completing the task or not selecting the practice), a degree of detail in the information, a degree of objectiveness, a strength of a recommendation in the information, etc.

At block 1010, information engine 340 determines, for each of one or more pieces of information, which information characteristic(s) the information piece is associated with. The determination can be performed based on, for example, one or more tags for the task, a keyword detection in the task and/or a source of the information piece.

At block 1015, task engine 345 can receive user input with a task preference and/or task constraint and/or information engine 340 can receive user input with an information preference and/or information constraint. The preference or constraint can be a positive one or a negative one. A preference can include a scaled response. For example, a user can identify a ranking (e.g., from 1-10) for an information characteristic, can order various characteristics in terms of preference, and/or can assign a weight to each of one or more characteristics.

At block 1020, task engine 345 accesses a user response provided in response to each of one or more questions probing condition-management approach decisions. In some instances, at least one question was provided as part of an account set up. In some instances, at least one question was presented as a task. A question may, for example, ask the user to identify a current condition-management decision (e.g., to identify vitamins being taken for the condition, to identify exercise practices, to identify a sleeping-pattern characteristic, etc.), to identify a plan for a future condition-management decision (e.g., to identify whether a pregnant woman is planning on an elective C-section or to identify a patient's interest or openness to select treatment options) or to identify a condition-management goal (e.g., a symptom that the patient particularly wants relief of, a labor pain threshold, or a risk tolerance). The question may be associated with binary response options (e.g., yes or no), a set of potential response options or a response scale. For example, a question may request that a user rank multiple condition goals in order of importance. As another example, a question may request that a user identify a numeric probability of selecting a particular condition-management decision in the future.

At block 1025, task engine 345 accesses influence data that associates presentation of particular pieces of information with task-completion data. In one instance, the influence data determines whether and/or how presentations of particular pieces of information are correlated with completion of one or more tasks. For example, it may be determined that presenting information associated with a particular information characteristic is correlated with high completion rates of tasks associated with a particular task characteristic. In one instance, the influence data determines whether and/or how presentations of particular pieces of information are correlated with particular completion characteristics. For example, it may be determined that presenting information associated with a particular information characteristic is correlated with receiving particular question responses. To specifically illustrate, presentation of information outlining potential dangers of co-sleeping may be associated with user responses identifying reduced interest in co-sleeping.

At block 1030, population manager 365 accesses outcome data identifying relationships between presentation of particular information pieces with intermediate or final condition results. For example, for a pregnancy condition, the intermediate or final condition result can include a pregnancy duration prior to birth, whether a labor was assisted, whether a C-section was performed, whether the infant survived, whether the infant was admitted into the NICU, whether the infant was diagnosed with any mental or physical conditions, whether the mother had an extended hospital stay, whether the mother was readmitted to the hospital for a reason related to the birth, a labor duration, whether an infant survived for at least a threshold duration (e.g., 1 month, 6 months, etc.), whether an infant died from SIDS or SUIDS, whether an infant developed to have any learning conditions, etc. For example, it may be determined that presentation to an expecting mother of two or more information pieces about SIDS risk factors is associated with a reduced risk of a SIDS death for her child.

Based on the input, user response, influence data and/or outcome data, an information-selection protocol can be set at block 1035. Setting the protocol can include adjusting a previous or default protocol. The protocol can be set to, for example, abide by user-input constraints, bias information-piece selection according to user-input preferences, bias towards selection of information pieces having a characteristic associated with high subsequent task completions, bias towards selection of information pieces having a characteristic associated with target user responses, and/or bias towards selection of information pieces having a characteristic associated with a positive intermediate or final condition result.

In some instances, an information-selection protocol includes selecting one or more information characteristics for a given user and then biasing an information-piece selection towards an information piece with the one or more information characteristics and/or requiring that a selected information piece be associated with the one or more information characteristics. In one instance, for a given user, each of one or more information characteristics is assigned a weight (e.g., based on data or input as discussed herein), and each information piece is assigned a score based on its association with each of the one or more information characteristics (e.g., which may be binary or non-binary) and the information-characteristic weight(s). An information-piece selection can then include, for example, pseudo-randomly selecting an information piece from amongst those assigned an above-threshold score, selecting a top- or high-score information piece that has not been presented to a particular user before, etc.

In some instances, a piece of information is selected based on a task selection or the converse. For example, information about the pros and/or cons of particular decisions can be presented prior to requesting that a user identify a predicted decision on the issue. As another example, a response to a question can influence what information is subsequently presented to the user. To illustrate, if a user indicates that she intends to have a home birth, information regarding the increased mortality rates associated with home births can be presented.

Figure 11:
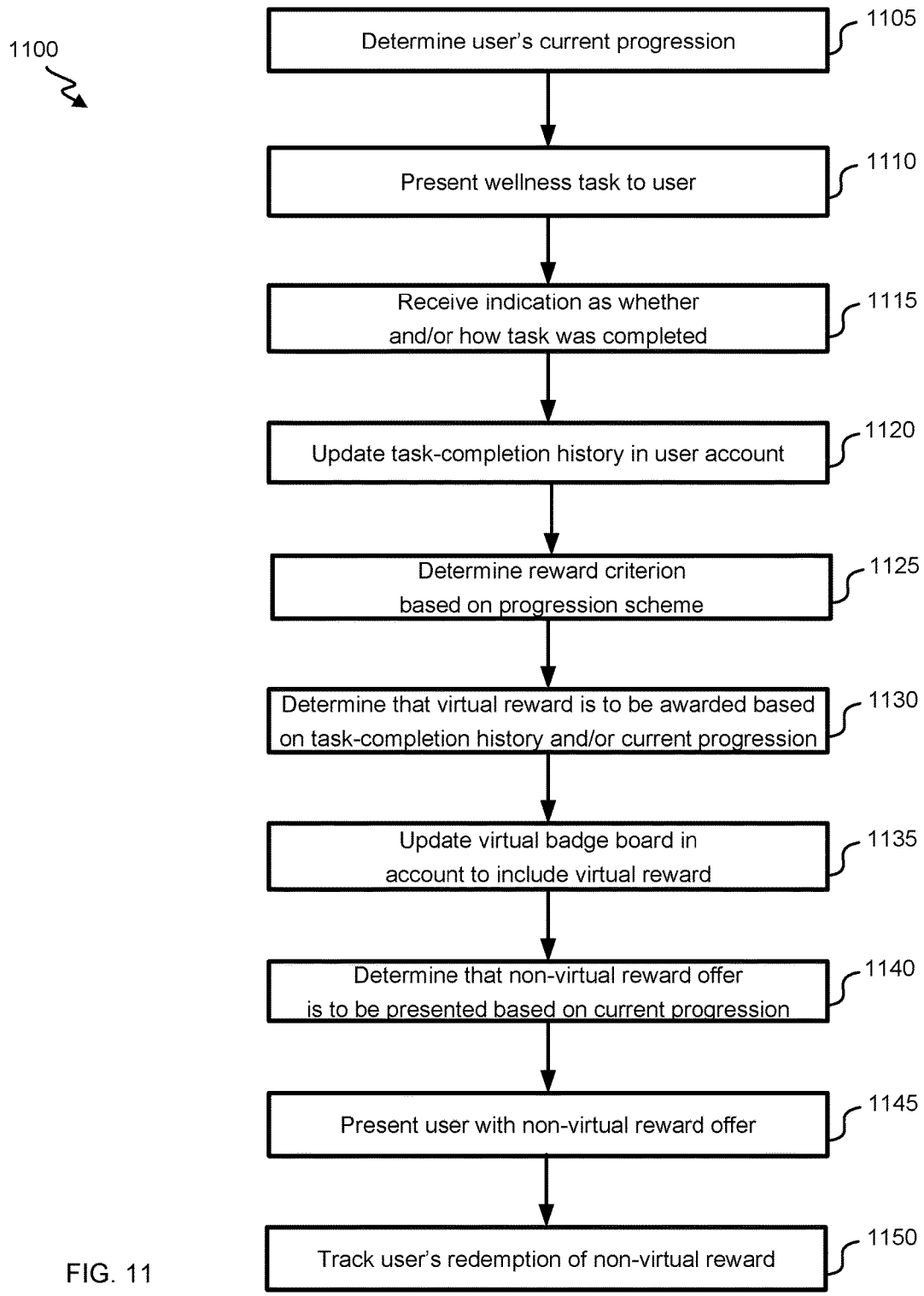
FIG. 11 illustrates a flowchart of an embodiment of a process for presenting virtual and non-virtual rewards to wellness app users.

FIG. 11 illustrates a flowchart of an embodiment of a process 1100 for presenting virtual and non-virtual rewards to wellness app users 103. Process 1100 begins at block 1105, where progression tracker 335 determines a current progression in a progression scheme of user 103. Task engine 345 presents a wellness task to user 103 at block 1110. The task can be one from a node for the current progression. Task engine 345 receives an indication from a user 103 as whether and/or how the task was completed at block 1115.

Task engine 345 updates task-completion history to reflect whether and/or how the task was completed in the user's account at block 1115. Reward manager 350 determines a reward criterion based on progression scheme at block 1125. The criterion can be a criterion for a virtual or non-virtual reward. In some instances, block 1125 involves determining criterion for each of a set of rewards (e.g., all potential rewards for a given scheme), which can include virtual and non-virtual rewards. The criterion can be related to a user's progression and/or task completions. The criterion can be defined, e.g., by an operator of system 150, a scheme manager 101 or a merchant 107.

At block 1130, reward manager 350 determines that virtual reward is to be awarded based on a criterion, which can relate to the task-completion history and potentially also the user's current progression. Reward manager 350 updates a virtual badgeboard of user's account to include virtual reward at block 1135. User 103 (and potentially other users) can view the badgeboard and then see the awarded virtual reward. In some instances, rather than adding the reward to a badgeboard, the reward is added to another virtual reward space, such as adding virtual points to a virtual score.

At block 1140, based on a criterion, reward manager 350 determines that non-virtual reward offer from value database is to be presented to user 103. The determination can be based on the user's current progression at block 1140 and, e.g., not on task completions. Thus, in this instance, a virtual reward is based on a user's task completions, while a non-virtual reward is not. Reward manager 350 presents user 103 with the non-virtual reward offer at block 1145. Reward manager 350 tracks whether and/or how the user redeems the non-virtual reward at block 1150. For example, the non-virtual reward can be a discount for purchases made on a merchant's website. Block 1150 can include determining whether a user clicks on a link in the offer to go to the website, whether the user makes a purchase once on the website and/or an amount of the purchase.

Figure 12:
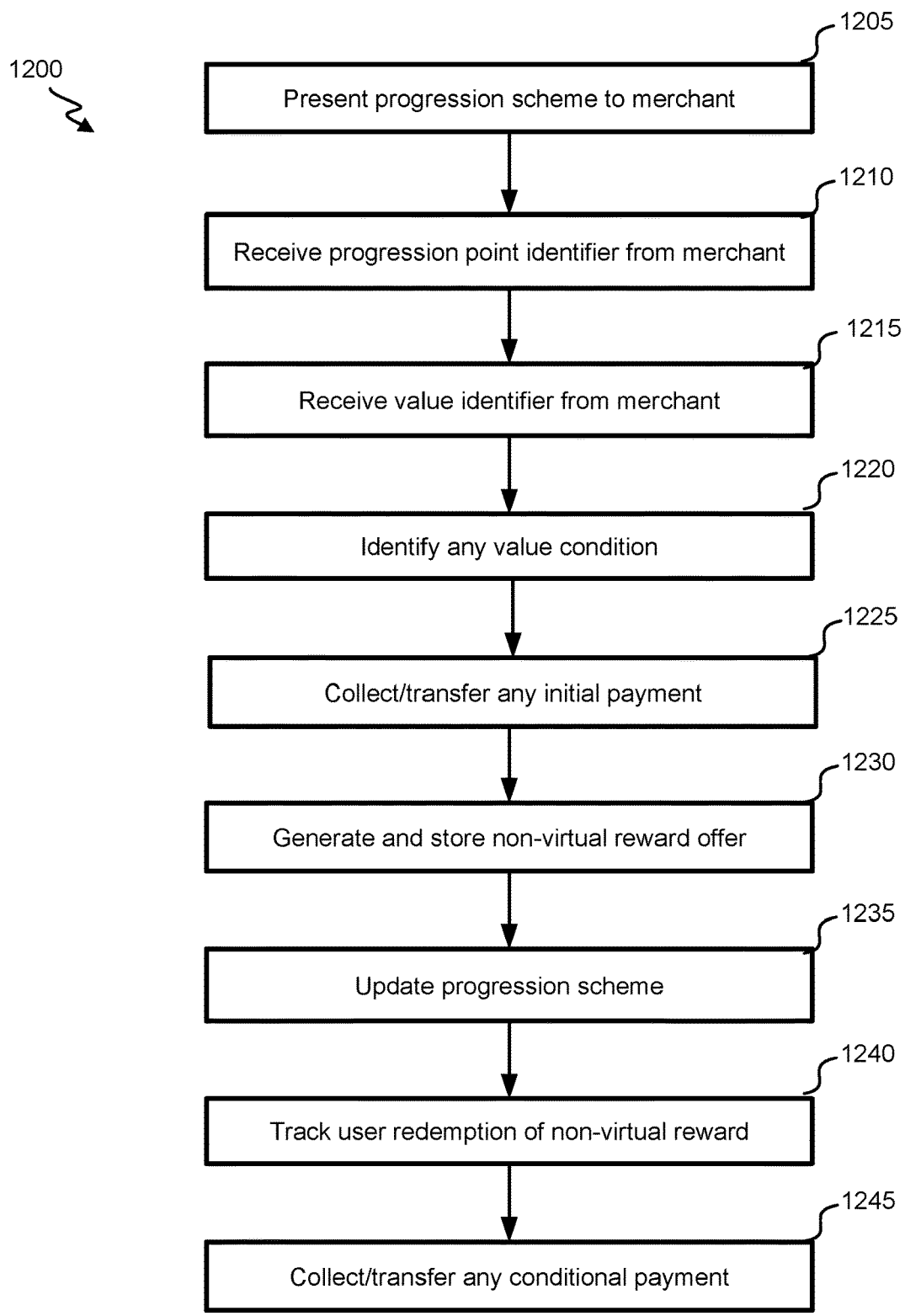
FIG. 12 illustrates a flowchart of an embodiment of a process for offering a non-virtual reward to app users provided by a merchant.

FIG. 12 illustrates a flowchart of an embodiment of a process 1200 for offering a non-virtual reward to app users 103 provided by a merchant 107. Process 1200 begins at block 1205, where merchant engine 360 presents a representation of a progression scheme to a merchant 107. The representation can identify nodes and progression criteria, such that merchant 107 can understand why and/or when a user 103 will be placed at one node versus another. In some instances, existing tasks, information and/or potential rewards are also identified to merchant 107, while in other instances, they are not.

Merchant engine 360 receives a progression point from merchant at block 1210. For example, the progression point can include a node or a transfer between nodes. Merchant engine 360 receives a value identifier from merchant at block 1215. The value identifier can identify a non-virtual reward (e.g., a discount amount, a voucher, a website/product/service for which the voucher or discount can be used, etc.). The value identifier can further include restrictions on the reward (e.g., an expiration date, minimum-purchase requirement, agreement to auto-subscribe to a service, etc.).

Merchant engine 360 identifies any value condition at block 1220. The condition can relate to use of system 150, user characteristics and/or task completions. For example, merchant 107 can specify that a non-virtual reward is only to be offered to users who have used system 150 for at least two weeks, are between the ages of 20 and 35 and have completed at least 5 exercise tasks.

Merchant engine 360 collects or transfers any initial payment at block 1225. In one instance, merchant 107 must pay system 150 before the merchant's non-virtual reward is offered to users. In one instance, system 150 pays merchant 107 for the reward offer. The payment can be made via electronic payment or by transferring credit-card information.

Merchant engine 360 generates a non-virtual reward offer based on the value identifier and stores the reward offer in value database 355 at block 1230. Scheme engine 305 updates progression scheme at block 1235. Specifically, an identification of the non-virtual reward offer and/or any associated conditions can be added to scheme nodes or node connections.

Reward manager 350 tracks users' redemption of the non-virtual reward at block 1240, The tracking can involve identifying how many users redeemed the reward, characteristics of users who redeemed the reward, and/or how users redeemed the reward (e.g., how much was purchased on a website while using an offered discount). The tracking can be performed using, e.g., a tracking code from the offer (which could be a discount or voucher code itself or a website). In some instances, tracking includes receiving data from a merchant or merchant's website reporting redemption characteristics.

Merchant engine 360 collects or transfers any conditional payment at block 1245. For example, system 150 may collect a defined or percentage fee (e.g., based on an amount purchased by a user while using a discount non-virtual reward) from merchant 107 for each user redeeming the fee or the converse. An amount or percentage of the fee may be fixed across users or may vary depending, e.g., on user characteristics or presentation characteristics (e.g., which node a user was at when the offer was presented or how many other offers were presented with the offer at issue).

It will be appreciated that, while process 1200 identifies how a merchant 107 can interact with system 150 to add a non-virtual reward, in some instances, no such direct system access is available to merchant 107. Instead, for example, an operator of system 150 and/or a scheme manager 101 can identify the non-virtual reward(s).

Figure 13:
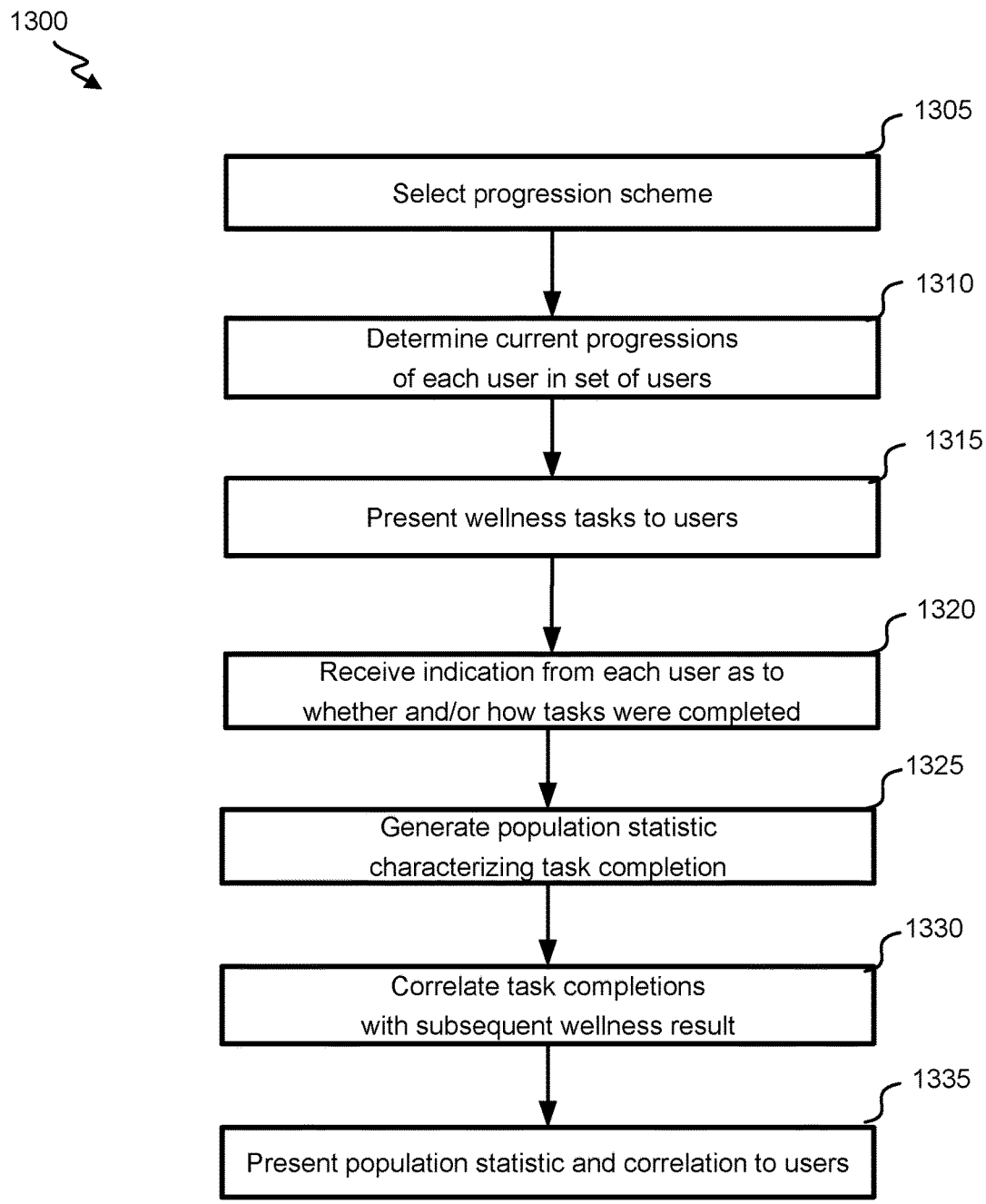
FIG. 13 illustrates a flowchart of an embodiment of a process for correlating app task completions with wellness results.

FIG. 13 illustrates a flowchart of an embodiment of a process 1300 for correlating app task completions with wellness results. Process 1300 begins at block 1305, where scheme engine 305 selects progression scheme from scheme database 310.

Using the progression scheme, progression tracker 335 determines a current progression of each user in a set of users at block 1310. For example, progression tracker 335 can position each user at a node in the scheme. The set of users can include, e.g., all users using system 150 for which a same progression scheme is being used. In some instances, the set is further restricted to only include users using the scheme within a given time period.

Task engine 345 presents one or more wellness tasks to each user in the set of users at block 1315. The number and/or identity of tasks presented can vary across the users and can depend on their scheme placements and progressions, time of placements, pseudo-random task selections, user characteristics, etc.

Task engine 345 receives an indication from each user as to whether and/or how each presented task was completed at block 1320. Population manager 365 generates a population statistic characterizing task completions at block 1325. The population statistic can relate to all tasks, tasks of various types (e.g., having a separate statistic for each type), or particular tasks (e.g., having a separate statistic for each task). The statistic can indicate a completion probability, a speed or completion following task presentation or an extent of completion.

Population manager 365 correlates the task completion (which can include whether the task was completed and/or an extent of the completion) with a subsequent wellness result at block 1330. The correlation can involve, e.g., determining significance and/or R or $R^2$ values and/or using a model. This correlation can be performed globally, separately for various task types, or separately for individual tasks. Thus, for example, the correlation can indicate whether users who completed any exercise task in the fifth month of their pregnancy were more likely to remain off of bed rest. In some instances, the correlation is sensitive to a number of completed tasks. For example, a model can indicate that completions of exercise tasks are correlated with full-term deliveries, that this correlation is stronger as a number of completed exercise tasks increases, though the correlation strength levels off at 5 task completions per week. The correlation can also account for potentially confounding factors, such as user characteristics.

Population manager 365 presents the population statistic and/or the correlation to a user at block 1335. The users to whom the statistic and/or correlation are presented to can include, e.g., all users, all users previously presented with a task of a particular type studied in the correlation, all users previously presented with a particular task studied in the correlation, and/or all users subsequently presented with a particular task of a task of a particular type studied in the correlation. For example, population manager 365 can present to a user who previously received a particular relaxation task, an indication that 75% of users completed the task, that the task was correlated with blood-pressure reduction, and that the user herself did not complete the task. As another example, population manager 365 can simultaneously present a choose-a-name-for-your-baby task to a user and indicate that 95% of users reported completing this task within a week from the task's presentation. As yet another example, on a user's account page, population manager 365 can indicate that, of those users who completed 15 or more tasks within a month, 95% of them achieve a weight-loss goal. A total task completion for the user can be simultaneously presented. As still a further example, population manager 365 can show a graph of a distribution among a group of 18-25 year-old users as to a number of tasks completed in the last month, with a first symbol at an x-position showing the user's task completions and a second symbol at an x-position showing an estimated optimal number of task completions for achieving a particular wellness result.

Figure 14:
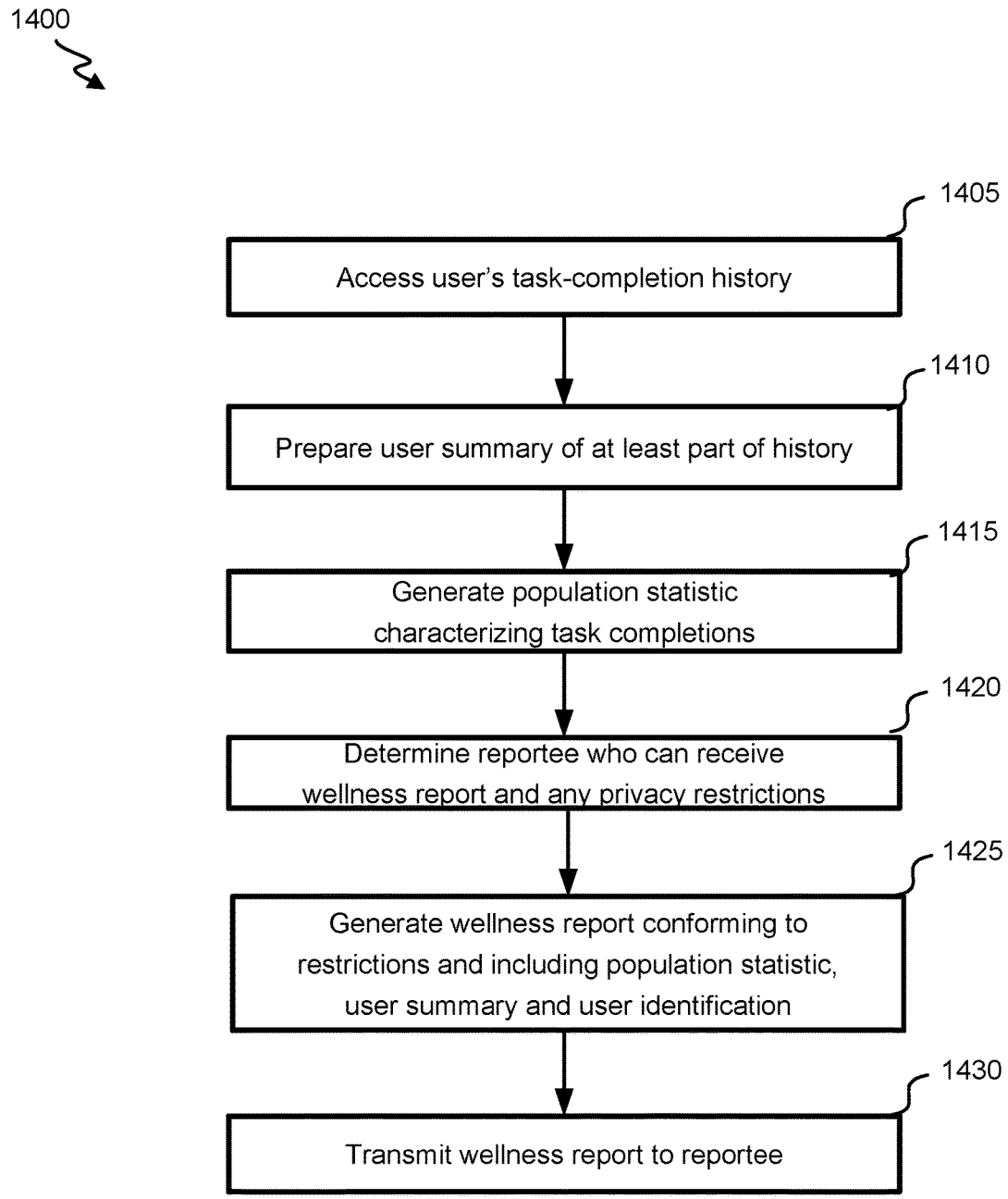
FIG. 14 illustrates a flowchart of an embodiment of a process for generating a report characterizing app task completions.

FIG. 14 illustrates a flowchart of an embodiment of a process 1400 for generating a report characterizing app task completions. Process 1400 begins at block 1405, where report engine 370 accesses a task-completion history in a user's account. The history can indicate which specific tasks and/or task types were presented to the user, which tasks and/or task types were completed by the user, a degree of any completion, when tasks were presented and/or when tasks were completed.

Report engine 370 prepares a user summary of at least part of the history at block 1410. For example, the user summary can indicate (e.g., globally or for one or more time periods): how many tasks were completed, how many tasks of each of one or more types were completed, how many tasks were presented, how many tasks of each of one or more types were presented, and/or a degree of the completions.

Population manager 365 generates a population statistic characterizing task completions at block 1415. The population statistic can relate to a number of tasks completed, a portion of tasks completed versus tasks presented, an identification of tasks or task types with various absolute completions or percent completions (given a number of task presentations). Thus, the population statistic can mirror the user summary. The population statistic can be generated based on all users or a group of users—such as those receiving similar task presentations as the users, those in a similar age bracket as the user, those with similar conditions or condition complications as the user, those having a same insurance provider as the user, those having a same insurance policy as the user and/or those having a same employer as the user.

Report engine 370 determines a reportee 109 who can receive wellness reports and any privacy restrictions at block 1420. Reportee 109 can be one expressly identified by user 103, one implicitly identified by user 103 (e.g., when she identified her insurance company, employer or physician for account data), a client of system 150 (e.g., paying to receive reports), a user 103 herself, a merchant 107, etc. In some instances, user 103 agreed to provide reports to reportee 109

(e.g., by agreeing to app terms of service, by responding to a specific report-permission request from a reportee 109, or by indicating the permission while identifying specific parties, such as a physician, employer or insurance company). In some instances, the user's identity is sufficiently obscured such that no permission is necessary.

Report engine 370 generates a wellness report conforming to privacy restrictions and including population statistic, user summary and user identification at block 1425. The privacy restrictions can include global restrictions of system 150, restrictions of system 150 specific to a user or group of users or restrictions identified by user 103. The restrictions can, e.g., restrict whether and/or to what extent the user can be identified in the report; which personal and/or health information can be included in the report; which account-interaction and/or task-completion information can be included in the report; which parties can receive the report; and/or how frequently one or more reportees 109 can receive the report. Thus, in some instances, the user identification is obscured (e.g., having an identifier number which may, or may not, be understood by a reportee 109 to correspond to a particular user). The report can include graphs, statistics, numbers and/or text and can be a file, email content, etc. Report engine 370 can store the report in report database 375.

Report engine 370 transmits wellness report to reportee 109 at block 1430. For example, a report file can be electronically sent to reportee 109 or the report can be sent within an email to reportee 109.

It will be appreciated that, in some instances, the transmitted wellness report includes the user summary identification and not the population summary or the population summary and not the user summary and user identification.

Figure 15:
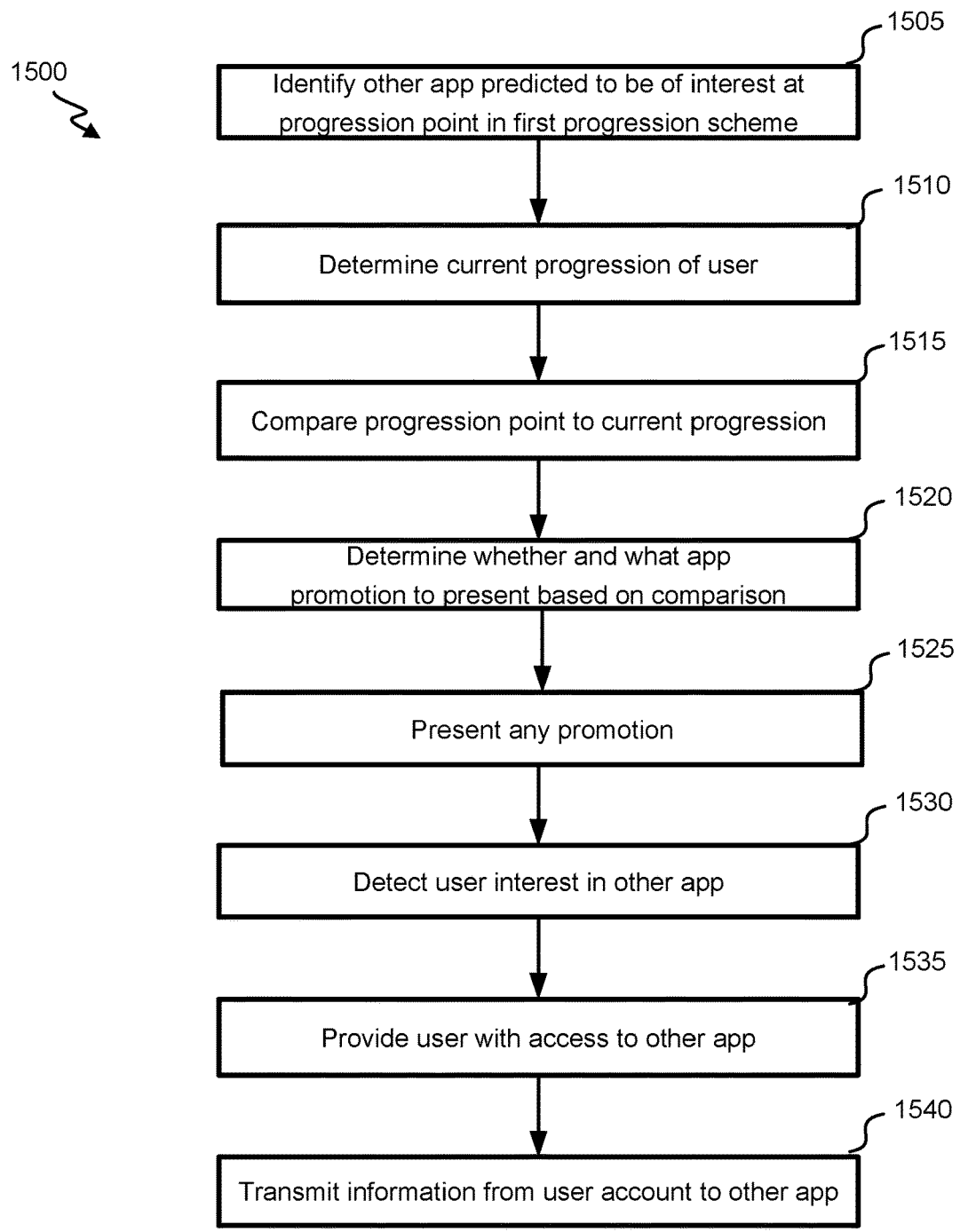
FIG. 15 illustrates a flowchart of an embodiment of a process for promoting an app at select scheme-progression points.

FIG. 15 illustrates a flowchart of an embodiment of a process 1500 for promoting an app at select scheme-progression points. Process 1500 begins at block 1505, where, based on a user's interaction with a first app, app promoter 380 identifies a second app predicted to be of interest at a progression point in a first scheme. The first app can be one provided by the partial or full operation of system 150, and (in some instances) the second app is controlled and operated by a separate system. The first app can be an app directed to improving wellness for a condition (e.g., pregnancy), and the second app can be one directed to improving wellness for a related condition or situation (e.g., postpartum or parenthood). In some instances, the second app is not directed to improving wellness.

Using the progression scheme, progression tracker 335 determines a current progression of user 103 at block 1510. App promoter 380 compares one or more progression points to the current progression at block 1515. The progression point(s) can be one(s) at which the second app is to be promoted. These points can be identified, e.g., based on a controller, manager or operator of a system for the second app or a scheme manager 101. The progression point(s) can include a node in the scheme, a time point (e.g., 5 weeks after first use of system 150 or 1 week from due date) or a time period (e.g., week 36 of pregnancy).

App promoter 380 determines whether and what app promotion to present any promotion based on comparison at block 1520. For example, if a progression point is the same, nearly the same as, or overlapping with the current progression, app promoter 380 can identify a promotion for that progression point. The promotion can include, e.g., an identification of the second app, a description of the second app, potentially desired features of the second app, an indication as to why the app is potentially of interest to the user (e.g., given her current interest in the first app or having a particular condition), information about how to obtain the app and/or an identification as to how the first and second apps can interact (e.g., by sharing information from the user's account in the first app with the second app).

If a promotion is to be presented, app promoter 380 presents the promotion at block 1525. The promotion can be presented to user 103 on a page of the first app, via an email or via a text message.

App promoter 380 detects interest by user 103 in the second app at block 1530. For example, a user 103 can selection an option on the promotion to have account information shared with the second app or to download the second app, or user 103 can click on a link pertaining to the second app (e.g., a download link).

App promoter 380 provides user with access to other app at block 1535. In some instances, app promoter 380 facilitates a download of the second app, e.g., by directing the user to a download site or by initiating the download. In some instances, app promoter 380 interacts with a system operating and/or controlling the second app as part of block 1535.

App promoter 380 transmits information from the user's account to second app at block 1540. The transmitted information can include, e.g., some or all of the user's health information, profile information, task-completion history, and/or virtual or non-virtual reward awardances. This information can be transmitted prior to or subsequent to download of the second app.

Figure 16:
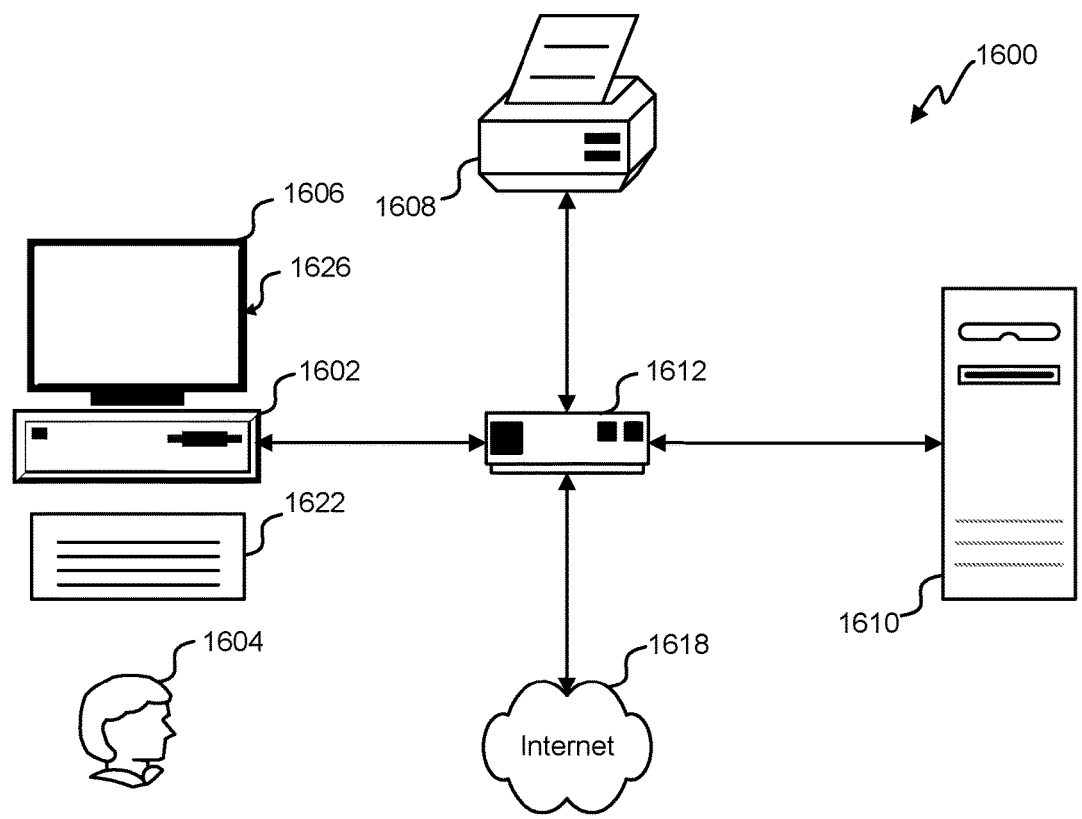
FIG. 16 depicts a block diagram of an embodiment of a computer system.

Referring next to FIG. 16, an exemplary environment with which embodiments can be implemented is shown with a computer system 1600 that can be used by a designer 1604 to design, for example, electronic designs. The computer system 1600 can include a computer 1602, keyboard 1622, a network router 1612, a printer 1608, and a monitor 1606. The monitor 1606, processor 1602 and keyboard 1622 are part of a computer system 1626, which can be a laptop computer, desktop computer, handheld computer, mainframe computer, etc. Monitor 1606 can be a CRT, flat screen, etc.

A designer 1604 can input commands into computer 1602 using various input devices, such as a mouse, keyboard 1622, track ball, touch screen, etc. If the computer system 1600 comprises a mainframe, a designer 1604 can access computer 1602 using, for example, a terminal or terminal interface. Additionally, computer system 1626 can be connected to a printer 1608 and a server 1610 using a network router 1612, which can connect to the Internet 1618 or a WAN.

Server 1610 can, for example, be used to store additional software programs and data. In one embodiment, software implementing the systems and methods described herein can be stored on a storage medium in server 1610. Thus, the software can be run from the storage medium in server 1610. In another embodiment, software implementing the systems and methods described herein can be stored on a storage medium in computer 1602. Thus, the software can be run from the storage medium in computer system 1626. Therefore, in this embodiment, the software can be used whether or not computer 1602 is connected to network router 1612. Printer 1608 can be connected directly to computer 1602, in which case, computer system 1626 can print whether or not it is connected to network router 1612.

Figure 17:
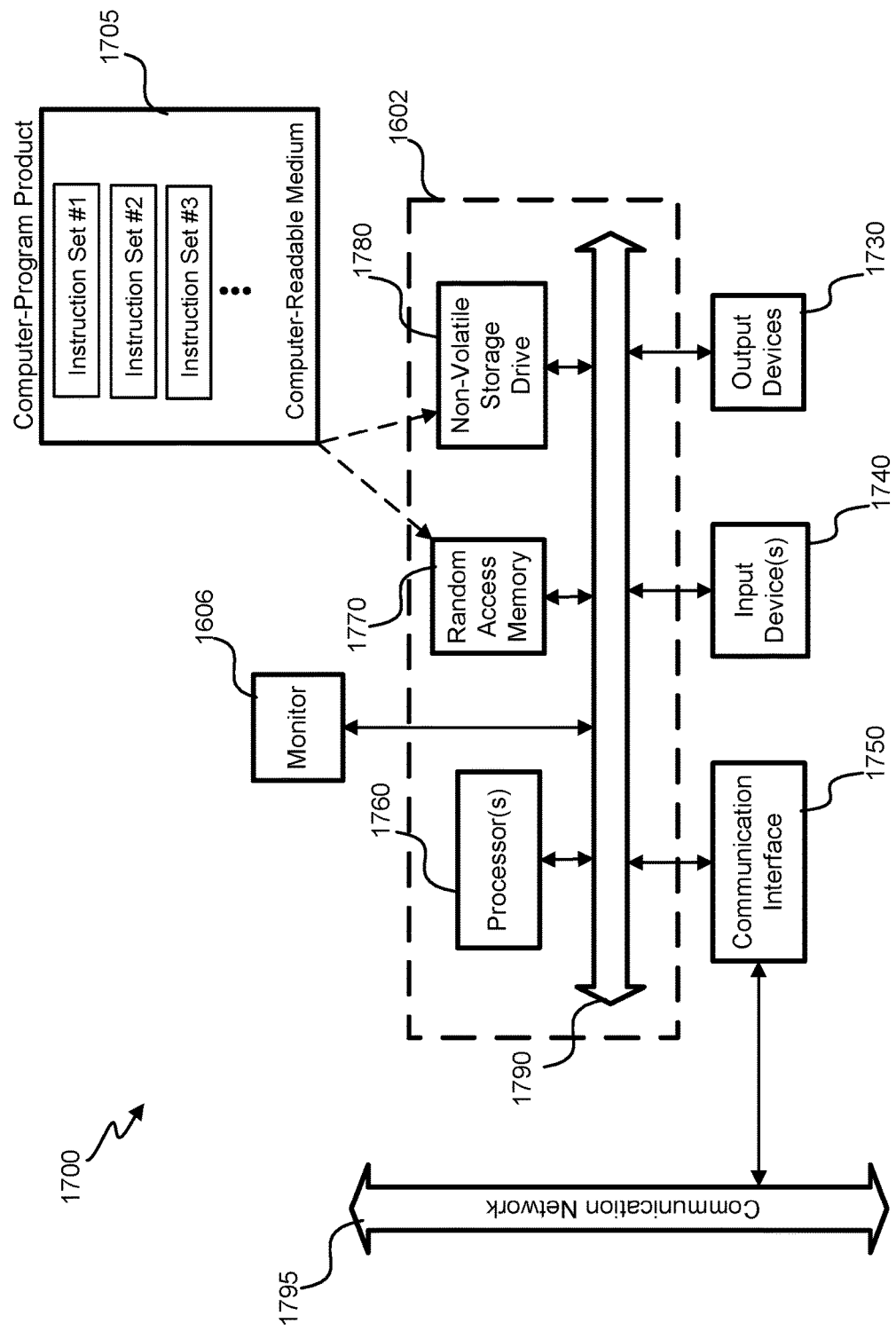
FIG. 17 depicts a block diagram of an embodiment of a special-purpose computer system.

With reference to FIG. 17, an embodiment of a special-purpose computer system 1700 is shown. Progressive wellness-promotion system 150 and/or any components thereof are examples of a special-purpose computer system 1700.

Thus, for example, one or more special-purpose computer systems 1700 can be used to provide the function of progressive wellness-promotion system 150. The above methods can be implemented by computer-program products that direct a computer system to perform the actions of the above-described methods and components. Each such computer-program product can comprise sets of instructions (codes) embodied on a computer-readable medium that directs the processor of a computer system to perform corresponding actions. The instructions can be configured to run in sequential order, or in parallel (such as under different processing threads), or in a combination thereof. After loading the computer-program products on a general purpose computer system 1626, it is transformed into the special-purpose computer system 1700.

Special-purpose computer system 1700 comprises a computer 1602, a monitor 1606 coupled to computer 1602, one or more additional user output devices 1730 (optional) coupled to computer 1602, one or more user input devices 1740 (e.g., keyboard, mouse, track ball, touch screen) coupled to computer 1602, an optional communications interface 1750 coupled to computer 1602, a computer-program product 1705 stored in a tangible computer-readable memory in computer 1602. Computer-program product 1705 directs system 1700 to perform the above-described methods. Computer 1602 can include one or more processors 1760 that communicate with a number of peripheral devices via a bus subsystem 1790. These peripheral devices can include user output device(s) 1730, user input device(s) 1740, communications interface 1750, and a storage subsystem, such as random access memory (RAM) 1770 and non-volatile storage drive 1780 (e.g., disk drive, optical drive, solid state drive), which are forms of tangible computer-readable memory.

Computer-program product 1705 can be stored in non-volatile storage drive 1790 or another computer-readable medium accessible to computer 1602 and loaded into memory 1770. Each processor 1760 can comprise a microprocessor, such as a microprocessor from Intel® or Advanced Micro Devices, Inc®, or the like. To support computer-program product 1705, the computer 1602 runs an operating system that handles the communications of product 1705 with the above-noted components, as well as the communications between the above-noted components in support of the computer-program product 1705. Exemplary operating systems include Windows® or the like from Microsoft Corporation, Solaris® from Sun Microsystems, LINUX, UNIX, and the like.

User input devices 1740 include all possible types of devices and mechanisms to input information to computer system 1602. These can include a keyboard, a keypad, a mouse, a scanner, a digital drawing pad, a touch screen incorporated into the display, audio input devices such as voice recognition systems, microphones, and other types of input devices. In various embodiments, user input devices 1740 are typically embodied as a computer mouse, a trackball, a track pad, a joystick, wireless remote, a drawing tablet, a voice command system. User input devices 1740 typically allow a user to select objects, icons, text and the like that appear on the monitor 1606 via a command such as a click of a button or the like. User output devices 1730 include all possible types of devices and mechanisms to output information from computer 1602. These can include a display (e.g., monitor 1606), printers, non-visual displays such as audio output devices, etc.

Communications interface 1750 provides an interface to other communication networks and devices and can serve as an interface to receive data from and transmit data to other systems, WANs and/or the Internet 1618. Embodiments of communications interface 1750 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1750 can be coupled to a computer network, to a FireWire® bus, or the like. In other embodiments, communications interface 1750 can be physically integrated on the motherboard of computer 1602, and/or can be a software program, or the like.

RAM 1770 and non-volatile storage drive 1780 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1770 and non-volatile storage drive 1780 can be configured to store the basic programming and data constructs that provide the functionality of various embodiments of the present invention, as described above.

Software instruction sets that provide the functionality of the present invention can be stored in RAM 1770 and non-volatile storage drive 1780. These instruction sets or code can be executed by processor(s) 1760. RAM 1770 and non-volatile storage drive 1780 can also provide a repository to store data and data structures used in accordance with the present invention. RAM 1770 and non-volatile storage drive 1780 can include a number of memories including a main random access memory (RAM) to store of instructions and data during program execution and a read-only memory (ROM) in which fixed instructions are stored. RAM 1770 and non-volatile storage drive 1780 can include a file storage subsystem providing persistent (non-volatile) storage of program and/or data files. RAM 1770 and non-volatile storage drive 1780 can also include removable storage systems, such as removable flash memory.

Bus subsystem 1790 provides a mechanism to allow the various components and subsystems of computer 1602 communicate with each other as intended. Although bus subsystem 1790 is shown schematically as a single bus, alternative embodiments of the bus subsystem can utilize multiple busses or communication paths within computer 1602.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A progressive wellness-promotion system for promoting wellness via customized task presentation in a wellness app, the progressive wellness-promotion system comprising:

a server system comprising at least one server coupled to one or more network interfaces to facilitate communications via a network, wherein the wellness app is provided to a user for installation on a mobile computing device that is remote from the server system and is associated with the user, the server system comprising:

a scheme engine that selects a progressive support scheme from a database of the server system that promotes wellness by encouraging a plurality of users to responsibly respond to a health condition, wherein the progressive support scheme includes a set of nodes, each node of the set of nodes representing a progression of the health condition and being associated with a set of tasks, each task of the set of tasks corresponding to a task characteristic of a plurality of task characteristics, the task characteristic including a type of task;

a progression tracker that identifies progress, for each user of the plurality of users and based at least in part on automatically detected data collected by the server system from a plurality of user devices that are associated with the plurality of users that comprise the mobile computing device, with respect to a current node from the set of nodes as corresponding to a current progression of the health condition for the plurality of users, the current node being associated with an associated set of tasks that corresponds to a set of task characteristics from amongst the plurality of task characteristics, such that, for each task characteristic of the set of task characteristics, at least one task in the set of tasks corresponds to the task characteristic, where the automatically detected data corresponds to each user device of the plurality of user devices automatically detecting sensor measurements of a corresponding sensor, the server system receiving the automatically detected data from the plurality of user devices;

a population manager that, based at least in part on the automatically detected data, generates a population statistic that indicates whether one or more other users of the plurality of users performed one or more tasks of the set of tasks, and correlates task completion of the set of tasks with one or more wellness result values corresponding to an objective attained by at least some of the plurality of users, where the scheme engine modifies the progressive support scheme based at least in part on the correlation;

a task engine that generates a transmission, the transmission comprising a piece of information, to the mobile computing device associated with the user based at least in part on:

assigning a weight to each task characteristic of the set of task characteristics, based at least in part on processing a previous transmission received via the network to determine an input received from the mobile computing device associated with the user, the input including an indication as to whether a previously presented task was performed;

automatically selecting one task characteristic from amongst the set of task characteristics associated with the current node based at least in part on the assigned weights;

identifying a subset of tasks associated with the current node, each task in the subset of tasks corresponding to the one task characteristic selected; and automatically identifying one task from amongst the subset of tasks as an identified task to be presented; and the server system to transmit a task notification via a wireless communication channel of the network to the mobile computing device associated with the user to present the population statistic indicating task completions of the plurality of users that performed one or more tasks of the set of tasks based at least in part on the automatically detected data.

2. The progressive wellness-promotion system of claim 1, where the generating the population statistic comprises:

accessing population task-performance data that indicates whether the one or more other users of the plurality of users performed the one or more tasks of the set of tasks; and assigning a weight to each task characteristic of the set of task characteristics, based at least in part on the population task-performance data.

3. The progressive wellness-promotion system of claim 1, where the identifying the progress comprises:

receiving an indication from at least one user device of the plurality of devices as to whether and/or how the one or more tasks were completed; and updating the population task-performance data based at least in part on the indication.

4. The progressive wellness-promotion system of claim 1, where the population statistic indicates a completion probability with respect to the set of tasks.

5. The progressive wellness-promotion system of claim 1, where the population statistic indicates a speed of task completion following a task presentation.

6. The progressive wellness-promotion system of claim 1, where the population statistic indicates an extent of completion with respect to the set of tasks.

7. The progressive wellness-promotion system of claim 1, where the population manager causes presentation of the population statistic and/or the correlation with the user devices of the plurality of user devices that have been previously caused to present the one or more tasks and/or that are subsequently caused to present the one or more tasks.

8. A method for promoting wellness via customized task presentation in a wellness app, the method comprising:

selecting a progressive support scheme from a database of a server system that promotes wellness by encouraging a plurality of users to responsibly respond to a health condition, wherein the progressive support scheme includes a set of nodes, each node of the set of nodes representing a progression of the health condition and being associated with a set of tasks, each task of the set of tasks corresponding to a task characteristic of a plurality of task characteristics, the task characteristic including a type of task;

receiving by the server system automatically detected data from the plurality of user devices;

identifying progress, for each user of the plurality of users and based at least in part on automatically detected data collected by the server system from a plurality of user devices that are associated with the plurality of users that comprise the mobile computing device, with respect to a current node from the set of nodes as corresponding to a current progression of the health condition for the plurality of users, the current node being associated with an associated set of tasks that corresponds to a set of task characteristics from amongst the plurality of task characteristics, such that, for each task characteristic of the set of task characteristics, at least one task in the set of tasks corresponds to the task characteristic, where the automatically detected data corresponds to each user device of the plurality of user devices automatically detecting sensor measurements of a corresponding sensor;

generating a population statistic that indicates whether one or more other users of the plurality of users performed one or more tasks of the set of tasks based at least in part on the automatically detected data;

generates a population statistic that indicates whether one or more other users of the plurality of users performed one or more tasks of the set of tasks based at least in part on the automatically detected data;

correlating task completion of the set of tasks with one or more wellness result values corresponding to an objective attained by at least some of the plurality of users, and modifying the progressive support scheme based at least in part on the correlation;

generating a transmission, the transmission comprising a piece of information, to a mobile computing device associated with a user based at least in part on:

assigning a weight to each task characteristic of the set of task characteristics, based at least in part on processing a previous transmission received via the network to determine an input received from the mobile computing device associated with the user, the input including an indication as to whether a previously presented task was performed;

automatically selecting one task characteristic from amongst the set of task characteristics associated with the current node based at least in part on the assigned weights;

identifying a subset of tasks associated with the current node, each task in the subset of tasks corresponding to the one task characteristic selected; and automatically identifying one task from amongst the subset of tasks as an identified task to be presented; and transmitting a task notification via a wireless communication channel of the network to the mobile computing device associated with the user to present the population statistic indicating task completions of the plurality of users that performed one or more tasks of the set of tasks based at least in part on the automatically detected data.

9. The method of claim 8, where the generating the population statistic comprises:

accessing population task-performance data that indicates whether the one or more other users of the plurality of users performed the one or more tasks of the set of tasks; and assigning a weight to each task characteristic of the set of task characteristics, based at least in part on the population task-performance data.

10. The method of claim 8, where the identifying the progress comprises:

receiving an indication from at least one user device of the plurality of devices as to whether and/or how the one or more tasks were completed; and updating the population task-performance data based at least in part on the indication.

11. The method of claim 8, where the population statistic indicates a completion probability with respect to the set of tasks.

12. The method of claim 8, where the population statistic indicates a speed of task completion following a task presentation.

13. The method of claim 8, where the population statistic indicates an extent of completion with respect to the set of tasks.

14. The method of claim 8, further comprising:
causing presentation of the population statistic and/or the correlation with the user devices of the plurality of user devices that have been previously caused to present the one or more tasks and/or that are subsequently caused to present the one or more tasks.

15. One or more non-transitory, machine-readable media having instructions stored thereon, which, when executed by one or more processing devices of a server system, cause the server system to perform:
selecting a progressive support scheme from a database of the server system that promotes wellness by encouraging a plurality of users to responsibly respond to a health condition, wherein the progressive support scheme includes a set of nodes, each node of the set of nodes representing a progression of the health condition and being associated with a set of tasks, each task of the set of tasks corresponding to a task characteristic of a plurality of task characteristics, the task characteristic including a type of task;
processing automatically detected data received by the server system from the plurality of user devices;
identifying progress, for each user of the plurality of users and based at least in part on automatically detected data collected by the server system from a plurality of user devices that are associated with the plurality of users that comprise the mobile computing device, with respect to a current node from the set of nodes as corresponding to a current progression of the health condition for the plurality of users, the current node being associated with an associated set of tasks that corresponds to a set of task characteristics from amongst the plurality of task characteristics, such that, for each task characteristic of the set of task characteristics, at least one task in the set of tasks corresponds to the task characteristic, where the automatically detected data corresponds to each user device of the plurality of user devices automatically detecting sensor measurements of a corresponding sensor;
generating a population statistic that indicates whether one or more other users of the plurality of users performed one or more tasks of the set of tasks based at least in part on the automatically detected data;
correlating task completion of the set of tasks with one or more wellness result values corresponding to an objective attained by at least some of the plurality of users, and modifying the progressive support scheme based at least in part on the correlation;
generating a transmission, the transmission comprising a piece of information, to a mobile computing device associated with a user based at least in part on:
assigning a weight to each task characteristic of the set of task characteristics, based at least in part on processing a previous transmission received via the network to determine an input received from the mobile computing device associated with the user, the input including an indication as to whether a previously presented task was performed;
automatically selecting one task characteristic from amongst the set of task characteristics associated with the current node based at least in part on the assigned weights;
identifying a subset of tasks associated with the current node, each task in the subset of tasks corresponding to the one task characteristic selected; and
automatically identifying one task from amongst the subset of tasks as an identified task to be presented; and
transmitting a task notification via a wireless communication channel of the network to the mobile computing device associated with the user to present the population statistic indicating task completions of the plurality of users that performed one or more tasks of the set of tasks based at least in part on the automatically detected data.

16. The one or more non-transitory, machine-readable media of claim 15, where the generating the population statistic comprises:
accessing population task-performance data that indicates whether the one or more other users of the plurality of users performed the one or more tasks of the set of tasks; and
assigning a weight to each task characteristic of the set of task characteristics, based at least in part on the population task-performance data.

17. The one or more non-transitory, machine-readable media of claim 15, where the identifying the progress comprises:
receiving an indication from at least one user device of the plurality of devices as to whether and/or how the one or more tasks were completed; and
updating the population task-performance data based at least in part on the indication.

18. The one or more non-transitory, machine-readable media of claim 15, where the population statistic indicates a completion probability with respect to the set of tasks.

19. The one or more non-transitory, machine-readable media of claim 15, where the population statistic indicates a speed of task completion following a task presentation.

20. The one or more non-transitory, machine-readable media of claim 15, where the population statistic indicates an extent of completion with respect to the set of tasks.

* * * * *